(12) United States Patent
Sheridan et al.

(10) Patent No.: US 9,789,111 B2
(45) Date of Patent: Oct. 17, 2017

(54) CASEIN KINASE 1δ (CK 1δ) INHIBITORS

(71) Applicant: Electrophoretics Limited, Cobham, Surrey (GB)

(72) Inventors: Joseph M. Sheridan, Cobham (GB); Jonathan R. Heal, Cobham (GB); William D. O. Hamilton, Cobham (GB); Ian H. Pike, Cobham (GB)

(73) Assignee: ELECTROPHORETICS LIMITED, Cobham Surrey (GB)

( * ) Notice: Subject to any disclaimer, the term of this patent is extended or adjusted under 35 U.S.C. 154(b) by 0 days.

(21) Appl. No.: 14/677,273

(22) Filed: Apr. 2, 2015

(65) Prior Publication Data

US 2015/0209368 A1  Jul. 30, 2015

Related U.S. Application Data

(62) Division of application No. 13/993,303, filed as application No. PCT/GB2011/052473 on Dec. 14, 2011.

(30) Foreign Application Priority Data

| Dec. 14, 2010 | (GB) | 1021161.3 |
| Jun. 1, 2011 | (GB) | 1109162.6 |

(51) Int. Cl.

| A61K 31/517 | (2006.01) |
| A61K 31/437 | (2006.01) |
| A61K 31/4439 | (2006.01) |
| A61K 31/506 | (2006.01) |
| C07D 209/42 | (2006.01) |
| C07D 277/68 | (2006.01) |
| C07D 401/04 | (2006.01) |
| C07D 401/12 | (2006.01) |
| C07D 403/06 | (2006.01) |
| C07D 405/04 | (2006.01) |
| C07D 405/12 | (2006.01) |
| C07D 407/12 | (2006.01) |
| C07D 413/06 | (2006.01) |
| C07D 413/14 | (2006.01) |
| C07D 471/04 | (2006.01) |
| C07D 487/04 | (2006.01) |
| C07D 487/14 | (2006.01) |
| C07D 495/14 | (2006.01) |
| A61K 31/397 | (2006.01) |
| A61K 31/4192 | (2006.01) |
| A61K 31/519 | (2006.01) |
| A61K 31/53 | (2006.01) |
| A61K 31/55 | (2006.01) |
| A61K 31/4045 | (2006.01) |
| A61K 31/444 | (2006.01) |

(52) U.S. Cl.
CPC ......... *A61K 31/517* (2013.01); *A61K 31/397* (2013.01); *A61K 31/4045* (2013.01); *A61K 31/4192* (2013.01); *A61K 31/437* (2013.01); *A61K 31/444* (2013.01); *A61K 31/4439* (2013.01); *A61K 31/506* (2013.01); *A61K 31/519* (2013.01); *A61K 31/53* (2013.01); *A61K 31/55* (2013.01); *C07D 209/42* (2013.01); *C07D 277/68* (2013.01); *C07D 401/04* (2013.01); *C07D 401/12* (2013.01); *C07D 403/06* (2013.01); *C07D 405/04* (2013.01); *C07D 405/12* (2013.01); *C07D 407/12* (2013.01); *C07D 413/06* (2013.01); *C07D 413/14* (2013.01); *C07D 471/04* (2013.01); *C07D 487/04* (2013.01); *C07D 487/14* (2013.01); *C07D 495/14* (2013.01)

(58) Field of Classification Search
None
See application file for complete search history.

(56) References Cited

U.S. PATENT DOCUMENTS

| 5,545,656 | A | 8/1996 | Loose et al. |
| 6,087,363 | A | 7/2000 | Longley et al. |
| 6,953,794 | B2 | 10/2005 | Wischik et al. |
| 8,697,627 | B2 | 4/2014 | Alam |
| 8,883,785 | B2 * | 11/2014 | Dominguez ......... C07D 401/04 514/235.8 |
| 9,427,438 | B2 | 8/2016 | Alam |
| 2003/0219427 | A1 | 11/2003 | Allen et al. |
| 2004/0014802 | A1 | 1/2004 | Dutruc-Rosset et al. |
| 2004/0235819 | A1 | 11/2004 | Galley et al. |
| 2009/0163545 | A1 | 6/2009 | Goldfarb |
| 2010/0029598 | A1 | 2/2010 | Kopitz et al. |
| 2010/0152157 | A1 | 6/2010 | Puech et al. |
| 2010/0179154 | A1 | 7/2010 | Almario Garcia et al. |

FOREIGN PATENT DOCUMENTS

| EP | 1636375 B1 | 8/2008 | |
| EP | 2149551 A1 | 2/2010 | |
| GB | WO 2011091153 A1 * | 7/2011 | ......... C07D 401/04 |
| WO | WO 0012497 A2 | 3/2000 | |
| WO | 0218386 A1 | 3/2002 | |
| WO | WO 0222606 A1 | 3/2002 | |
| WO | 02051821 A1 | 7/2002 | |
| WO | 03051833 A2 | 6/2003 | |
| WO | 03076398 A2 | 9/2003 | |
| WO | 03106439 A1 | 12/2003 | |

(Continued)

OTHER PUBLICATIONS

ICD-9-CM Tabular List of Diseases (FY03) on the Washington University School of Medicine in St. Louis website Online "http://gamma.wustl.edu/division/icd9tbp.pdf" accessed Sep. 10, 2015.*

(Continued)

*Primary Examiner* — David K O'Dell
(74) *Attorney, Agent, or Firm* — Arent Fox LLP

(57) ABSTRACT

The invention relates to pharmaceutical compositions having casein kinase 1 delta (CK1δ) inhibitors and to the use of the inhibitors in the treatment of neurodegenerative disorders such as Alzheimer's disease.

8 Claims, 5 Drawing Sheets

(56) References Cited

FOREIGN PATENT DOCUMENTS

| WO | WO 2004078733 A1 | 9/2004 | |
| WO | 2005001114 A2 | 1/2005 | |
| WO | WO 2005099711 A1 | 10/2005 | |
| WO | 2007110243 A1 | 10/2007 | |
| WO | WO 2007149448 A2 * | 12/2007 | ........... C07D 241/18 |
| WO | 2008041140 A3 | 4/2008 | |
| WO | 2008052907 A1 | 5/2008 | |
| WO | 2008058402 A1 | 5/2008 | |
| WO | 2008077138 A1 | 6/2008 | |
| WO | 2009073141 A2 | 6/2009 | |
| WO | WO 2010018327 A1 | 2/2010 | |
| WO | 2010130934 A2 | 11/2010 | |

OTHER PUBLICATIONS

"Alzheimer's disease and tauopathy" University of Cambridge John van Geest Centre for Brain Repair School of Clinical Medicine Online "http://www.brc.cam.ac.uk/research/alzheimers-disease-and-tauopathy/" accessed Sep. 10, 2015.*

Tomohiro Chiba "Emerging Therapeutic Strategies in Alzheimer's Disease" Intech 2013.*

Mullard "Pharma pumps up anti-tau Alzheimer pipeline despite first Phase III failure" Nature Reviews Drug Discovery vol. 15 Sep. 2016, 591-592.*

Sergeant "Different distribution of phosphorylated tau protein isoforms in Alzheimer's and Pick's diseases" FEBS Letters 412 (1997) 578-582.*

Mendoza "Global Analysis of Phosphorylation of Tau by the Checkpoint Kinases Chk1 and Chk2 in vitro" J. Proteome Res. 2013, 12, 2654-2665.*

Lee, V. et al., "Neurodegenerative Tauopathies", Annual Review of Neuroscience, vol. 24, 2001, pp. 1121-1159.

Ghoshal, N. et al., "A New Molecular Link between the Fibrillar and Granulovacuolar Lesions of Alzheimer's Disease", American Journal of Pathology, vol. 155, No. 4, Oct. 1999, pp. 1163-1172.

Yasojima, K. et al., "Casein kinase 1 delta mRNA is upregulated in Alzheimer disease brain", Brain Research, vol. 865, 2000, pp. 116-120.

Kuret, J. et al., "Casein Kinase 1 is Tightly Associated with Paired-Helical Filaments Isolated from Alzheimer's Disease Brain", Journal of Neurochemistry, vol. 69, No. 6, 1997, pp. 2506-2515.

Li, G. et al., "Casein Kinase 1 Delta Phosphorylates Tau and Disrupts Its Binding to Microtubules", Journal of Biological Chemistry, vol. 279, pp. 15938-15945.

Chauhan, A. et al., "Amyloid β-protein stimulates casein kinase I and casein kinase II activities", Brain Research, vol. 629, 1993, pp. 47-52.

Flajolet, M. et al., "Regulation of Alzheimer's disease amyloid-β formation by casein kinase I", PNAS, vol. 104, No. 10, Mar. 6, 2007, pp. 4159-4164.

Hanger, D. et al., "Novel Phosphorylation Sites in Tau from Alzheimer Brain Support a Role for Casein Kinase 1 in Disease Pathogenesis", Journal of Biological Chemistry, vol. 282, No. 32, Aug. 10, 2007, pp. 23645-23654.

Berge, S. et al., "Pharmaceutical Salts", Journal of Pharmaceutical Sciences, vol. 66, No. 1, Jan. 1977, pp. 1-19.

Flunkert, S. et al., "Elevated Levels of Soluble Total and Hyperphosphorylated Tau Result in Early Behavioral Deficits and Distinct Changes in Brain Pathology in a New Tau Transgenic Mouse Model", Neurodegenerative Diseases, vol. 11, 2013, pp. 194-205.

Loeffler, T. et al., "Stable Mutated tau441 Transfected SH-SY5Y Cells as Screening Tool for Alzheimer's Disease Drug Candidates", J. Mol Neurosci, vol. 47, 2012, pp. 192-203.

Andreani, A. et al., "Synthesis and Screening for Antiacetylcholinesterase Activity of (1-Benzyl-4-oxopiperidin-3-ylidene)methylindoles and -pyrroles Related to Donepezil", Journal of Medicinal Chemistry, vol. 44, No. 23, 2001, pp. 4011-4014.

Bain, J. et al., "The selectivity of protein kinase inhibitors: a further update", Biochem. J., vol. 408, 2007, pp. 297-315.

Bain, J. et al., "The specificities of protein kinase inhibitors: an update", Biochem. J., vol. 371, 2003, pp. 199-204.

Bamborough, P. et al., "Assessment of Chemical Coverage of Kinome Space and Its Implications for Kinase Drug Discovery", Journal of Medicinal Chemistry, vol. 51, No. 24, 2008, pp. 7898-7914.

Chem Abs XP002670846—2005, Database accession No. 4480043.
Chem Abs XP002670847—2005, Database accession No. 4101452.
Chem Abs XP002677911—2007, Database Registry 938032-58-7.
Chem Abs XP002677912—2006, Database Registry 889940-39-0.

Fabian, M. et al., "A small molecule-kinase interaction map for clinical kinase inhibitors", Nature Biotechnology, vol. 23, No. 3, Mar. 2005, pp. 329-336.

Lemercier, G. et al., "Identification and Characterization of Novel Small Molecules as Potent Inhibitors of the Plasmodial Calcium-Dependent Protein Kinase 1", Biochemistry, vol. 48, No. 27, Jun. 2009, pp. 6379-6389.

Mashhoon, N. et al., "Crystal Structure of a Conformation-selective Casein Kinase-1 Inhibitor", Journal of Biological Chemistry, vol. 275, No. 26, Jun. 30, 2000, pp. 20052-20060.

Meijer, L. et al., "Inhibition of cyclin-dependent kinases, GSK-3β and CK1 by hymenialdisine, a marine sponge constituent", Chemistry & Biology, vol. 7, No. 1, 2000, 51-63

Perez, D. et al., "Protein Kinases CK1 and CK2 as New Targets for Neurodegenerative Diseases", Medicinal Research Reviews, DOI: 10.1002/med.20207 (www.interscience.wiley.com), 2010, pp. 1-31.

Voigt, B. et al., "Probing Novel 1-Aza-9-oxafluorenes as Selective GSK-3β Inhibitors", ChemMedChem, vol. 3, 2008, pp. 120-126.

Yuzawa, S. et al., "O—GlcNAc and neurodegeneration: biochemical mechanisms and potential roles in Alzheimer's disease and beyond", Chem. Soc. Rev., vol. 43, 2014, pp. 6839-8853.

Hook, V., "Neuroproteases in Peptide Neurotransmission and Neurodegenerative Diseases", Biodrugs, vol. 20, No. 2, 2006, pp. 105-119.

Jhee, S. et al., "β-Amyloid therapies in Alzheimer's disease", Expert Opinion on Investigational Drugs, vol. 10, No. 4, 2001, pp. 593-605.

D'Onofrio, G. et al., "Advances in the identification of γ-secretase inhibitors for the treatment of Alzheimer's disease", Expert Opinion Drug Discovery, vol. 7, No. 1, 2012, pp. 19-37.

Iqbal, K. et al., "Microtubule-associated protein tau as a therapeutic target in Alzheimer's disease", Expert Opinion Ther. Targets, vol. 18, No. 3, 2014, pp. 307-318.

STN-Chemical database registry # RN 889940-39-0, 2-amino-3-(4-fluorobenzoyl)-1-Indolizinecarboxamide Jun. 29, 2006.

ChemBlock, online: "http://web.archive.org/web/20051204015543/http://www.chemblock.com/screening.php" dated Dec. 4, 2005, accessed Dec. 2, 2014.

"http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Nov. 9, 2011.

Thomas, D., PCT International Search Report, PCT/GB2011/052473 dated Jul. 3, 2012, 13 pages.

Li, G. et ai., "Casein Kinase 1 Delta Phosphorylates Tau and Disrupts Its Binding to Microtubules", The Journal of Biological Chemistry, vol. 279, Apr. 16, 2004, pp. 15938-15945.

Henze, H. et al., "The Number of Structurally Isomeric Alcohols of The Methanol Series", Journal of the American Chemical Society, vol. 53, Aug. 1931, pp. 3042-3046.

Patani, G.A. et al., "Bioisosterism: A Rational Approach in Drug Design", Chemical Reviews, vol. 96, No. 8, 1996, pp. 3147-3176.

Wakefield, B., "Fluorinated Pharmaceuticals" Innovations in Pharmaceutical Technology 2003, pp. 74, 76-78, Online "http://web.archive.org/web/20030905122408/http://www.iptonline.com/articles/public/IPTFOUR74NP.pdf." (accessed via Wayback machine Nov. 20, 2009 showing web availability as of Sep. 2003).

http://web.archive.org/web/20100930184751/http://www.princetonbio.com/pages4.html dated Sep. 30, 2010, accessed Apr. 30, 2015.

(56) References Cited

OTHER PUBLICATIONS 2-amino-3-(2-thienylcarbonyl)-1-Indolizinecarboxamide, RN 919984-20-6 entered in the STN database ChemCats Feb. 8, 2007.
2-amino-3-(4-chlorobenzoyl)-1-Indolizinecarboxamide, RN 889950-00-9 entered in the STN database ChemCats Jun. 29, 2006.
Corcoran, Niall M. et al., "Sodium selenate specifically activates PP2A phosphatase, dephosphorylates tau and reverses memory deficits in an Alzheimer's disease model", Journal of Clinical Neuroscience, vol. 17, Apr. 2010, pp. 1025-1033.
Götz, Jürgen, et al., "Tau Filament Formation in Transgenic Mice Expressing P301L Tau", The Journal of Biological Chemistry, vol. 276, No. 1, Jan. 5, 2001, pp. 529-534.
"TauRx Publishes Positive Results of Phase II Clinical Trial in the Journal of Alzheimer's Disease", Press Release, Jan. 20, 2015.
"EIP Pharma announces positive results with neflamapimod (VX-745) in two Phase 2a clinical trials in patients with Early Alzheimer's Disease", Dec. 8, 2016, 6 pages.
Roberson, Erik D., et al., "Reducing Endogenous Tau Ameliorates Amyloid b-Induced Deficits in an Alzheimer's Disease Mouse Model", Science, vol. 316, May 4, 2007, pp. 750-754.
Roberson, Erika, "Mouse Models of Frontotemporal Dementia", Ann Neural. Dec. 2012, vol. 72, Issue 6, pp. 837-849.
Trojanowski, John Q., "Tau-focused therapy and tau transmission: Implications for Alzheimer's Disease and related tauopathies", Oral Presentation, Molecular Neurodegeneration: Basic biology and disease pathways Cannes, France. Sep. 10-12, 2013, 1 page.
Van Eersel, Janet, "Sodium selenate mitigates tau pathology, neurodegeneration, and functional deficits in Alzheimer's disease models", PNAS, vol. 107, No. 31, Aug. 3, 2010, pp. 13888-13893.
Wang, Jun, et al., "Grape Derived Polyphenols Attenuate Tau Neuropathy in a Mouse Model of Alzheimer's Disease", Journal of Alzheimer's Disease, vol. 22, 2010, pp. 653-661.
Wang, Yipeng et al., "Tau in physiology and pathology", Nature Reviews Neuroscience, vol. 17, Jan. 2016, pp. 5-21.
Götz, Jürgen, et al., "Animal models of Alzheimer's disease and frontotemporal dementia", Nature Reviews Neuroscience, vol. 9, Jul. 2008, pp. 532-546.
"Akos Screening Samples ca. 3.5 million compounds Version Dec. 7, 2007" Online http://web.archive.org/web/20071219115313/http://www.akosgmbh.de/AKosSamples/index.html dated Dec. 7, 2007, accessed Sep. 29, 2015.
Chemical Abstract No. XP002671271, dated Jul. 16, 2005.
Chemical Abstract No. XP055021648, dated Dec. 28, 2008.
Chemical Abstract No. XP055021654, dated Sep. 13, 2002.
Thomas, D., PCT International Search Report, PCT/GB2011/052475, dated Jun. 21, 2012, 10 pages.

* cited by examiner

CASEIN KINASE 1δ (CK 1δ) INHIBITORS

CROSS-REFERENCE TO RELATED APPLICATIONS

This application is a divisional that claims priority to U.S. application Ser. No. 13/993,303 filed on Oct. 1, 2013, which is the U.S. national stage application of International Patent Application No. PCT/GB2011/052473 filed on Dec. 14, 2011, which claims priority to GB Application No. 1021161.3 filed on Dec. 14, 2010 and GB Application No. 1109162.6 filed on Jun. 1, 2011.

FIELD OF THE INVENTION

The invention relates to pharmaceutical compositions comprising casein kinase 1 delta (CK1δ) inhibitors and to the use of said inhibitors in the treatment of neurodegenerative disorders such as Alzheimer's disease.

BACKGROUND OF THE INVENTION

Alzheimer's disease (AD; also known as senile dementia of the Alzheimer type (SDAT), primary degenerative dementia of the Alzheimer's type (PDDAT), or Alzheimer's) is the most common form of dementia. Most often, Alzheimer's disease is diagnosed in people over 65 years of age, although the less-prevalent early-onset Alzheimer's can occur much earlier. In 2006, there were 26.6 million sufferers worldwide. Alzheimer's is predicted to affect 1 in 85 people globally by 2050.

Alzheimer's disease is a neurodegenerative disease characterised by the presence of senile plaques and neurofibrillary tangles in the brain. The degree of dementia at death correlates better with neurofibrillary tangle numbers than with senile plaques counts. The presence of neurofibrillary tangles in neurons results in the death of those neurons, implying that prevention of tangle formation is an important therapeutic goal. The principal protein that forms the neurofibrillary tangle is the microtubule-associated protein, tau, which assembles into filaments that have the appearance of twisting about each other in pairs and are referred to as paired helical filaments (PHF). PHF are present in different locations in degenerating neurons in the Alzheimer brain and when many aggregate in the neuronal cell body, they produce the neurofibrillary tangle (Lee et al, 2001).

Intraneuronal deposits of tau in the form of typical neurofibrillary tangles of AD or other morphologically distinct tau aggregates in a number of other neurodegenerative diseases, is the basis for grouping these conditions as tauopathies. Thus, in addition to AD, the main examples of the tauopathies are frontotemporal dementia with Parkinsonism linked to chromosome 17 (FTDP-17), progressive supranuclear palsy (PSP), Pick's disease, corticobasal degeneration, and multisystem atrophy (MSA). The intracellular tau deposits (usually neuronal but can also be glial) are all filamentous and mostly in a hyperphosphorylated state compared to the level of phosphorylation of tau from control human brain. In the case of AD, this hyperphosphorylated tau is often referred to as PHF-tau because it is derived from the PHF.

Tau is a phosphoprotein, the function of phosphorylation remaining to be unequivocally established. However, increased phosphorylation of tau on multiple serine and threonine residues reduces the ability of tau to promote microtubule assembly and to stabilise assembled microtubules, effects that have been demonstrated both in vitro and in cells. Many studies have shown that PHF-tau from AD brain is more heavily phosphorylated on serine and threonine than tau from control brain. This has been demonstrated partly by protein sequencing and partly by demonstrating that certain monoclonal antibodies only label either PHF-tau or non-phosphorylated tau and not PHF-tau; the epitopes for many of these antibodies have been mapped to particular phosphorylated residues present in PHF-tau and absent from control brain tau. The pathological tau from most other cases of other tauopathies seems to be similarly hyperphosphorylated to PHF-tau.

These findings strongly imply that similar abnormalities in regulating phosphorylation of tau are shared by all the tauopathies including AD.

A number of proline-directed and non-proline directed protein kinases have been suggested to have a role in the generation of PHF-tau in Alzheimer brain, including casein kinase 1. Mammalian casein kinase-1 exists as multiple isoforms CK1α, CK1β, CK1γ1, CK1γ2, CK1γ3, CK1δ and CK1ε. The role of CK1δ as a potential tau kinase is of particular interest since it has been reported that CK1δ protein is increased more than 30-fold in the hippocampus of Alzheimer brain compared to equivalent controls (Ghoshal, N. et al (1999) Am. J. Pathol 155, 1163-1172) while its mRNA content is increased 24-fold (Yasojima, K. et al (2000) Brain Res 865, 116-120) and CK1 has also been shown to be tightly associated with PHF (Kuret, J. et al (1997) J. Neurochem 69, 2506-2515). CK1δ has also been reported to phosphorylate tau at two epitopes detecting using phospho-specific monoclonal antibodies to tau, and exogenous expression of CK1δ in non-neuronal cells reduces binding of tau to microtubules (Li, G. et al (2004) J. Biol. Chem. 279, 15938-15945). Of note in the context of Alzheimer's disease is a report that CK1 activity is stimulated by amyloid beta-peptide (Aβ), a component of the senile neuritic plaques that, together with tangles, characterise Alzheimer brain (Chauhan, A. et al (1993) Brain Res. 629, 47-52). Additional evidence for possible involvement of CK1 in Alzheimer's disease comes from the reported influence of CK1 in the regulation of Aβ production in neurons (Flajolet, M. et al (2007) PNAS USA 104, 4159-4164). Further work has confirmed that at least 6 newly identified phosphorylation sites in PHF-tau (all on serine or threonine residues) can be generated by CK1δ. The finding that a number of phosphorylation sites in PHF-tau for which CK1 is a strong candidate kinase, including three for which it is the only known kinase, implies that CK1 may make an important contribution to the pathogenesis of Alzheimer's disease (Hanger et al (2007) J. Biol. Chem. 282, 23645-23654).

There is therefore a need for CK1δ inhibitors which may be of potential therapeutic benefit in the treatment of neurodegenerative diseases, such as tauopathies including Alzheimer's disease, frontotemporal dementia with Parkinsonism linked to chromosome 17 (FTDP-17), progressive supranuclear palsy (PSP), Pick's disease, corticobasal degeneration, and multisystem atrophy (MSA).

BRIEF SUMMARY OF THE INVENTION

In certain aspects, the invention is directed to a pharmaceutical composition comprising a compound of formula (IB) or a pharmaceutically acceptable salt or solvate thereof:

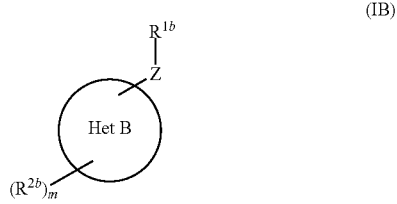

(IB)

wherein
"Het B" represents benzoxazolyl;
Z represents a bond;
$R^{1b}$ represents pyrimidinyl, wherein $R^{1b}$ may be substituted by one or more $R^{4b}$ groups;
$R^{4b}$ represents halogen, $C_{1-6}$ alkyl, $C_{1-6}$ alkenyl, $C_{1-6}$ alkynyl, $C_{3-8}$ cycloalkyl, halo$C_{1-6}$ alkyl, hydroxyl, $C_{1-6}$ alkoxy, —O—$C_{1-6}$ alkenyl, halo$C_{1-6}$ alkoxy, —COOH, —CO—$C_{1-6}$ alkyl, —COO—$C_{1-6}$ alkyl, —CONH$_2$, —CH$_2$—CONH$_2$, —NH—$C_{1-6}$ alkyl, —NH—$C_{2-6}$ alkenyl, —NH—CO—$C_{1-6}$ alkyl, —CO—NH—$C_{1-6}$ alkyl, —O—CH$_2$—CO—NH—$C_{1-6}$ alkyl, —CH$_2$—CH$_2$—CO—NH—$C_{1-6}$ alkyl, —S—$C_{1-6}$ alkyl, —SO—$C_{1-6}$ alkyl, —SO$_2$—$C_{1-6}$ alkyl, —SO$_2$—NH$_2$, —SO$_2$—NH—$C_{1-6}$ alkyl, —S—CH$_2$—CO—$C_{2-6}$alkenyl, —SO$_2$—OH, amino, cyano, NO$_2$, =O, —CO—NH—(CH$_2$)$_2$)—OMe, —NH—$C_{3-8}$ cycloalkyl, —CH$_2$—CO—NH—$C_{3-8}$ cycloalkyl, —CO-heterocyclyl, —CO— heteroaryl, —COO—(CH$_2$)$_2$-heterocyclyl, —CH$_2$-aryl, —OCH$_2$-aryl, —OCH$_2$-heteroaryl, —CH$_2$—O—CO -aryl, —O-aryl, —NH—CO-aryl, —NH—CO-heteroaryl, —NH—CO—CH$_2$-aryl, —NH-aryl, aryl, heterocyclyl or heteroaryl groups, wherein the aryl, heterocyclyl or heteroaryl groups of $R^{4b}$ may be optionally substituted by one or more halogen, $C_{1-6}$ alkyl, $C_{1-6}$ alkoxy, =S or hydroxyl groups and wherein the $C_{1-6}$ alkyl or $C_{2-6}$ alkenyl groups of $R^{4b}$ may be optionally substituted by one or more hydroxyl, amino, cyano, $C_{1-6}$ alkoxy, CONH$_2$ or —COO—$C_{1-6}$ alkyl groups;
m represents an integer from 0 to 3;
$R^{2b}$ represents halogen, halo$C_{1-6}$ alkyl, $C_{1-6}$ alkyl, $C_{3-8}$ cycloalkyl, hydroxyl, $C_{1-6}$ alkoxy, —S—$C_{1-6}$ alkyl, —CH$_2$—S—$C_{1-6}$ alkyl, —S—$C_{2-6}$ alkynyl, amino, cyano, NO$_2$, =O, =S, —SO$_2$—$C_{1-6}$ alkyl, —CONH$_2$, —CO—$C_{1-6}$ alkyl, —COO—$C_{1-6}$ alkyl, —NH—$C_{1-6}$ alkyl, —NH—CO—$C_{1-6}$ alkyl, —NH—CO—CH=CH—CH$_2$—N(Me)$_2$, $C_{1-6}$ alkyl, —CO—NH—$C_{1-6}$ alkyl, —CO—NH—CH(Me)-COOH, —S—CH$_2$—CO—N(Et)$_2$, —NH—(CH$_2$)$_2$—OH, —NH—(CH$_2$)$_3$—OH, —NH—CH(Et)-CH$_2$—OH, —CO—NH—(CH$_2$)$_3$—OH, —CH(CH$_2$OH)$_2$ or —S—CH$_2$—CO—NH—CO—NH—$C_{1-6}$ alkyl, wherein the $C_{1-6}$ alkyl groups of $R^{2b}$ may be optionally substituted by one or more cyano or hydroxyl groups.

In other aspects, the invention is directed to a method of using a pharmaceutical composition, for example, as described above, comprising: administering a therapeutically effective amount of the pharmaceutical composition in therapy. In yet other aspects, the invention is directed to a method of treating a neurodegenerative disorder comprising: administering a therapeutically effective amount of a pharmaceutical composition, for example, as described above, wherein the pharmaceutical composition is used as a casein kinase delta (CK1δ) inhibitor for the treatment of the neurodegenerative disorder.

DETAILED DESCRIPTION OF THE INVENTION

According to a first aspect of the invention there is provided a pharmaceutical composition comprising a compound of formula (IB) or a pharmaceutically acceptable salt or solvate thereof:

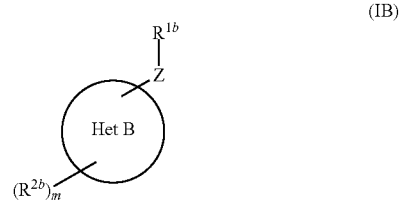

(IB)

wherein
"Het B" represents a 5 membered heterocyclic ring system containing 1 to 3 heteroatoms selected from O, N or S, wherein said ring system is fused to one or more (e.g. 1-3) further rings to form a polycyclic ring system comprising up to 4 rings;
Z represents a bond, —C($R^{7b}$)($R^{8b}$)—, (CH$_2$)$_2$, —O—, —S—, —CH$_2$—O—, —(CH$_2$)$_2$—O—, NR$^{6b}$, —N($R^{6b}$)—C($R^{7b}$)($R^{8b}$)—, —N($R^{6b}$)—(CH$_2$)$_2$—, —N($R^{6b}$)—(CH$_2$)$_3$—, —CH$_2$—N($R^{6b}$)—(CH$_2$)$_2$—, —N($R^{6b}$)—CO—, —CH$_2$—NH—CO—(CH$_2$)$_2$—, —N($R^{6b}$)—CO—CH$_2$—, =N—, —N($R^{7b}$)—CH=, —C(H)(CN)—, —C(=N—NH—COC$_{1-6}$alkyl)-, —CH=C($R^{6b}$)—CO—, =CH—, —N=CH—, —N=C(Me)-, —C($R^{6b}$)=CH—, —NH—CO—C(=CH-heteroaryl)-, —C(=C($R^{7b}$)($R^{8B}$)), CH=CH—CO—N($R^{6b}$)—, —CH=C($R^{6b}$)—CO—NH—CH$_2$—, —CH=C($R^{6b}$)—NH—CO—, —CH=C($R^{6b}$)—CO—O—CH$_2$—, —CS—S—CH$_2$—, —NH—CS—NH—, —NH—CS—NH—CH$_2$—, —NH—CS—NH—(CH$_2$)$_2$—, —CH$_2$—N(CSNH$_2$)—CH$_2$—, —S—C($R^{5b}$)($R^{6b}$)—, —S—(CH$_2$)$_2$—O—, SO$_2$, —NH—SO$_2$—, —CH$_2$—NH—SO$_2$—, CO, —CH$_2$—CO—, —(CH$_2$)$_2$—CO—, —O—CH$_2$—CO—, —(CH$_2$)$_2$—CO—, COO, —COO—C($R^{7b}$)CO—, —CH=C($R^{5b}$)—CONH—CH$_2$—, —CO—CH$_2$—N($R^{6b}$)—CO—, —CO—CH$_2$—C($R^{6b}$)—CH$_2$—CO—, —CO—CH$_2$—N($R^{6b}$)—CH$_2$—, —CO—NH—N=C($R^{7b}$)—, —S—CH$_2$—CO—, —S—CH$_2$—CO—N($R^{6b}$)—, —S—CH$_2$—CO—N($R^{6b}$)—CH$_2$—, —SO$_2$—N($R^{6b}$)—C($R^{7b}$)($R^{8b}$)—CONH—, —SO$_2$—N($R^{6b}$)—CH(—CH$_2$-aryl)-CONH—CH$_2$—, —CH(—S—C$_{1-6}$ alkyl) -C(Me)(OH)—, —CH$_2$—C($R^{6b}$)(OH)—, —C(OH)(CH(Me)(C$_{3-8}$ cycloalkyl))—CH$_2$—, —C(OH)($R^{6b}$)—CH$_2$—, —CH(Me)-NH—CO—CH$_2$—, —CO—N($R^{6b}$)—CH$_2$—, —C(H)($R^{6b}$)—CO—N($R^{5b}$)—CH$_2$—, —CO—N($R^{6b}$)—CH$_2$—CH$_2$—, —CO—N($R^{6b}$)—CH$_2$—CH$_2$—CO—NH—CH$_2$—, —CO—NH—C(=CONH$_2$)=CH—, —CO—NH—CH(—CONH$_2$)—CH$_2$—, —CH$_2$—C(H)(Me)-CH$_2$—S—, —O—CH$_2$—CO—NH—, —CH$_2$—N($R^{6b}$)—CO—CH$_2$—O—, —N($R^{6b}$)—CO—CH$_2$—O—, —C(H)(—CH$_2$-aryl)-, —C(H)(—CH$_2$-heteroaryl)-, —C(NH-aryl)=N—N=CH—, —C(NH-aryl)=N—N=CH—, —NH—CO—CH$_2$—N($R^{6b}$)—, —NH—N=C(-aryl)-, —NH—N=C(-aryl)—CO—, —NH—C(=N—CO—C$_{1-6}$alkyl)-NH—(CH$_2$)$_2$—, —C(—NH-aryl)=N—N=CH—, —NH—C(—NH-aryl)=N—CONH—, —C(=CH-aryl)-CONH—CH$_2$—, —CH=C($R^{6b}$)—CONH—, —CH(—CH₂-aryl)-NH—CO— or —CH(OH)—, wherein said aryl or heteroaryl groups of Z may be optionally substituted by one or more halogen, $C_{1-6}$ alkyl, $C_{1-6}$ alkoxy, $NO_2$ or hydroxyl groups;

$R^{5b}$ represents hydrogen, $C_{1-6}$ alkyl or cyano;

$R^{6b}$ represents hydrogen, $C_{1-6}$ alkyl, $C_{1-6}$ alkoxy, cyano, COOH, —COO$C_{1-6}$ alkyl, $C_{3-8}$ cycloalkyl, —CH₂—$C_{3-8}$ cycloalkyl, aryl, heteroaryl, —$C_{1-6}$ alkylene-aryl, —CO-aryl, —O—CO-heteroaryl, —CO-heteroaryl or —C($R^{7b}$)($R^{8b}$)-heteroaryl, wherein said aryl groups of $R^{6b}$ may be optionally substituted by one or more halogen or $C_{1-6}$ alkoxy groups;

$R^{7b}$ and $R^{8b}$ independently represent hydrogen or $C_{1-6}$ alkyl;

$R^{1b}$ represents aryl, $C_{3-8}$ cycloalkyl, monocyclic or bicyclic heterocyclyl or a monocyclic or bicyclic heteroaryl ring system, wherein $R^{1b}$ may be substituted by one or more (e.g. 1, 2 or 3) $R^{4b}$ groups;

$R^{4b}$ represents halogen, $C_{1-6}$ alkyl, $C_{1-6}$ alkenyl, $C_{1-6}$ alkynyl, $C_{3-8}$ cycloalkyl, halo$C_{1-6}$ alkyl, hydroxyl, $C_{1-6}$ alkoxy, —O—$C_{1-6}$ alkenyl, halo$C_{1-6}$ alkoxy, —COOH, —CO—$C_{1-6}$ alkyl, —COO—$C_{1-6}$ alkyl, —CONH₂, —CH₂—CONH₂, —NH—$C_{1-6}$ alkyl, —NH—$C_{2-6}$ alkenyl, —NH—CO—$C_{1-6}$ alkyl, —CO—NH—$C_{1-6}$ alkyl, —O—CH₂—CO—NH—$C_{1-6}$ alkyl, —CH₂—CH₂—CO—NH—$C_{1-6}$ alkyl, —S—$C_{1-6}$ alkyl, —SO—$C_{1-6}$ alkyl, —SO₂—$C_{1-6}$ alkyl, —SO₂—NH₂, —SO₂—NH—$C_{1-6}$ alkyl, —S—CH₂—CO—$C_{2-6}$ alkenyl, —SO₂—OH, amino, cyano, $NO_2$, =O, —CO—NH—(CH₂)₂—OMe, —NH—$C_{3-8}$ cycloalkyl, —CH₂—CO—NH—$C_{3-8}$ cycloalkyl, —CO-heterocyclyl, —CO-heteroaryl, —COO—(CH₂)₂-heterocyclyl, —CH₂-aryl, —OCH₂-aryl, —OCH₂-heteroaryl, —CH₂—O—CO-aryl, —O-aryl, —NH—CO-aryl, —NH—CO-heteroaryl, —NH—CO—CH₂-aryl, —NH-aryl, aryl or heteroaryl groups, wherein said aryl, heterocyclyl or heteroaryl groups of $R^{4b}$ may be optionally substituted by one or more halogen, $C_{1-6}$ alkyl, $C_{1-6}$ alkoxy, =S or hydroxyl groups and wherein said $C_{1-6}$ alkyl or $C_{2-6}$ alkenyl groups of $R^{4b}$ may be optionally substituted by one or more hydroxyl, amino, cyano, $C_{1-6}$ alkoxy, CONH₂ or —COO—$C_{1-6}$ alkyl groups;

m represents an integer from 0 to 3;

$R^{2b}$ represents halogen, halo$C_{1-6}$ alkyl, $C_{1-6}$ alkyl, $C_{3-8}$ cycloalkyl, hydroxyl, $C_{1-6}$ alkoxy, —S—$C_{1-6}$ alkyl, —CH₂—S—$C_{1-6}$ alkyl, —S—$C_{2-6}$ alkynyl, amino, cyano, $NO_2$, =O, =S, —SO₂—$C_{1-6}$ alkyl, —CONH₂, —CO—$C_{1-6}$ alkyl, —COO—$C_{1-6}$ alkyl, —NH—$C_{1-6}$ alkyl, —NH—CO—$C_{1-6}$ alkyl, —NH—CO—CH=CH—CH₂—N(Me)₂, $C_{1-6}$ alkyl, —CO—NH—$C_{1-6}$ alkyl, —CO—NH—CH(Me)-COOH, —S—CH₂—CO—N(Et)₂, —NH—(CH₂)₂—OH, —NH—(CH₂)₃—OH, —NH—CH(Et)-CH₂—OH, —CO—NH—(CH₂)₃—OH, —CH(CH₂OH)₂ or —S—CH₂—CO—NH—CO—NH—$C_{1-6}$ alkyl, wherein said $C_{1-6}$ alkyl groups of $R^{2b}$ may be optionally substituted by one or more cyano or hydroxyl groups;

with the proviso that the compound is other than compound number 54, 373, 458, 496, 585, 590, 594, 596-597, 601-602, 649, 703, 778, 877, 891, 910, 912, 926 and 962-963.

According to one particular aspect of the invention which may be mentioned there is provided a compound of formula (IB) or a pharmaceutically acceptable salt or solvate thereof:

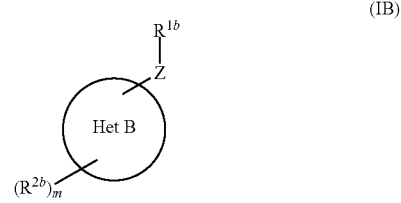

(IB)

wherein

"Het B" represents a 5 membered heterocyclic ring system containing 1 to 3 heteroatoms selected from O, N or S, wherein said ring system is fused to one or more (e.g. 1-3) further rings to form a polycyclic ring system comprising up to 4 rings;

Z represents a bond, —C($R^{7b}$)($R^{8b}$)—, —(CH₂)₂, —O—, —S—, CH₂—O—, —(CH₂)₂—O—, $NR^{6b}$, —N($R^{6b}$)—C($R^{7b}$)($R^{8b}$)—, —N($R^{6b}$)—(CH₂)₂—, —N($R^{6b}$)—(CH₂)₃—, —CH₂—N($R^{6b}$)—(CH₂)₂—, —N($R^{6b}$)—CO—, —CH₂—NH—CO—(CH₂)₂—, —N($R^{6b}$)—CO—CH₂—, =N—, —C(H)(CN)—, —C(=N—NH—CO$C_{1-6}$ alkyl)-, —CH=C($R^{6b}$)—CO —, =CH—, —N=CH—, —N=C(Me)-, —C($R^{6b}$)=CH—, —NH—CO—C(=CH-heteroaryl)-, —C—C(Me)₂-, —CH=CH—CO—N($R^{6b}$)—, —CH=C($R^{6b}$)—CO—NH—CH₂—, —CH=C($R^{6b}$)—NH—CO—, —CH=C ($R^{6b}$)—CO—O—CH₂—, —CS—S—CH₂—, —NH—CS—NH—, —NH—CS—NH—CH₂—, —NH—CS—NH—(CH₂)₂—, —CH₂—N(CSNH₂)—CH₂—, —S—C ($R^{5b}$)($R^{6b}$), S—(CH₂)₂—O—, SO₂, —NH—SO₂—, —CH₂—NH—SO₂—, CO, —CH₂—CO —, —(CH₂)₂—CO—, —O—CH₂—CO—, —(CH₂)₂—CO—, COO, —COO—C($R^{7b}$)CO—, —CH=C($R^{5b}$)—CONH—CH₂—, —CO—CH₂—N($R^{6b}$)—CO —, —CO—CH₂—C($R^{6b}$)—CH₂—CO—, —CO—CH₂—N($R^{6b}$)—CH₂—, —CO—NH—N=C($R^{7b}$)—, —S—CH₂—CO—, —S—CH₂—CO—N($R^{6b}$)—, —S—CH₂—CO—N ($R^{6b}$)—CH₂—, —SO₂—N($R^{6b}$)—C($R^{7b}$)($R^{8b}$)—CONH—, —SO₂—N($R^{6b}$)—CH(—CH₂-aryl)-CONH—CH₂—, —CH(—S—$C_{1-6}$ alkyl)-C(Me)(OH)—, —CH₂—C($R^{6b}$)(OH)—, —C(OH)(CH(Me)($C_{3-8}$ cycloalkyl))—CH₂—, —C(OH)($R^{6b}$)—CH₂—, —CH (Me)-NH—CO—CH₂—, —CO—N($R^{6b}$)—CH₂—, —C(H)($R^{6b}$)—CO—N($R^{5b}$)—CH₂—, —CO—N($R^{6b}$)—CH₂—CH₂—, —CO—N($R^{6b}$)—CH₂—CH₂—CO—NH—CH₂—, —CO—NH—C(—CONH₂)=CH—, —CO—NH—CH(—CONH₂)—CH₂—, —CH₂—C(H)(Me)-CH₂—S—, —O—CH₂—CO—NH—, —CH₂—N ($R^{6b}$)—CO—CH₂—O—, —N($R^{6b}$)—CO—CH₂—O—, —C(H)(—CH₂-aryl)-C(H)(—CH₂-heteroaryl)-, —C(NH-aryl)=N—N=CH—, —C(NH-aryl)=N—N=CH—, —NH—CO—CH₂—N($R^{6b}$)—, —NH—N=C(-aryl)-, —NH—N=C(-aryl) -CO—, —NH—C(=N—CO—$C_{1-6}$ alkyl)-NH—(CH₂)₂—, —C(—NH-aryl)=N—N=CH—, —NH—C(—NH-aryl)=N—CONH—, —C(=CH-aryl)-CONH—CH₂—, —CH=C($R^{6b}$)—CONH—, —CH(—CH₂-aryl)-NH—CO— or —CH (OH)—, wherein said aryl or heteroaryl groups of Z may be optionally substituted by one or more halogen, $C_{1-6}$ alkyl, $C_{1-6}$ alkoxy, $NO_2$ or hydroxyl groups;

$R^{5b}$ represents hydrogen, $C_{1-6}$ alkyl or cyano;

$R^{6b}$ represents hydrogen, $C_{1-6}$ alkyl, $C_{1-6}$ alkoxy, cyano, COOH, —COO$C_{1-6}$ alkyl, $C_{3-8}$ cycloalkyl, —CH₂—$C_{3-8}$ cycloalkyl, aryl, heteroaryl, —$C_{1-6}$ alkylene-aryl, —CO-aryl, —O—CO-heteroaryl, —CO— heteroaryl or —C($R^{7b}$)($R^{8b}$)-heteroaryl, wherein said aryl groups of $R^{6b}$ may be optionally substituted by one or more halogen or $C_{1-6}$ alkoxy groups;

$R^{7b}$ and $R^{8b}$ independently represent hydrogen or $C_{1-6}$ alkyl;

$R^{1b}$ represents aryl, $C_{3-8}$ cycloalkyl, monocyclic or bicyclic heterocyclyl or a monocyclic or bicyclic heteroaryl ring system, wherein $R^{1b}$ may be substituted by one or more (e.g. 1, 2 or 3) $R^{4b}$ groups;

$R^{4b}$ represents halogen, $C_{1-6}$ alkyl, $C_{1-6}$ alkenyl, $C_{1-6}$ alkynyl, $C_{3-8}$ cycloalkyl, halo$C_{1-6}$ alkyl, hydroxyl, $C_{1-6}$ alkoxy, —O—$C_{1-6}$ alkenyl, halo$C_{1-6}$ alkoxy, —COON, —CO—$C_{1-6}$ alkyl, —COO—$C_{1-6}$ alkyl, —CONH$_2$, —CH$_2$—CONH$_2$, —NH—$C_{1-6}$ alkyl, —NH—$C_{2-6}$ alkenyl, —NH—CO—$C_{1-6}$ alkyl, —CO—NH—$C_{1-6}$ alkyl, —O—CH2-CO—NH— $C_{1-6}$ alkyl, —CH$_2$—CH$_2$—CO—NH—$C_{1-6}$ alkyl, —S—$C_{1-6}$ alkyl, —SO—$C_{1-6}$ alkyl, —SO$_2$—$C_{1-6}$ alkyl, —SO$_2$—NH—$C_{1-6}$ alkyl, —S—CH$_2$—CO—$C_{2-6}$ alkenyl, —SO$_2$—OH, amino, cyano, NO$_2$, =O, —CO—NH—(CH$_2$)$_2$—OMe, —NH—$C_{3-8}$ cycloalkyl, —CH$_2$—CO—NH—$C_{3-8}$ cycloalkyl, —CO-heterocyclyl, —CO-heteroaryl, —COO—(CH$_2$)$_2$-heterocyclyl, —OCH$_2$-aryl, —OCH$_2$-heteroaryl, —CH$_2$—O—CO-aryl, —O-aryl, —NH—CO-aryl, —NH—CO-heteroaryl, —NH—CO—CH$_2$-aryl, —NH-aryl, aryl or heteroaryl groups, wherein said aryl, heterocyclyl or heteroaryl groups of $R^{4b}$ may be optionally substituted by one or more halogen, $C_{1-6}$ alkyl, $C_{1-6}$ alkoxy, =S or hydroxyl groups and wherein said $C_{1-6}$ alkyl or $C_{2-6}$ alkenyl groups of $R^{4b}$ may be optionally substituted by one or more hydroxyl, amino, cyano, $C_{1-6}$ alkoxy, CONH$_2$ or —COO—$C_{1-6}$ alkyl groups;

m represents an integer from 0 to 3;

$R^{2b}$ represents halogen, halo$C_{1-6}$ alkyl, $C_{1-6}$ alkyl, hydroxyl, $C_{1-6}$ alkoxy, —S—$C_{1-6}$ alkyl, —CH$_2$—S—$C_{1-6}$ alkyl, —S—$C_{2-6}$ alkynyl, amino, cyano, NO$_2$, =O, =S, —SO$_2$—$C_{1-6}$ alkyl, —CONH$_2$, —CO—$C_{1-6}$ alkyl, —COO—$C_{1-6}$ alkyl, —NH—$C_{1-6}$ alkyl, —NH—CO—$C_{1-6}$ alkyl, —NH—CO—CH=CH—CH$_2$—N(Me)$_2$, $C_{1-6}$ alkyl, —CO—NH—$C_{1-6}$ alkyl, —CO—NH—CH(Me)-COOH, —S—CH$_2$—CO—N(Et)$_2$, —NH—(CH$_2$)$_2$—OH, —NH—(CH$_2$)$_3$—OH, —NH—CH(Et)-CH$_2$—OH, —CO—NH—(CH$_2$)$_3$—OH, —CH(CH$_2$OH)$_2$ or —S—CH$_2$—CO—NH—CO—NH—$C_{1-6}$ alkyl, wherein said $C_{1-6}$ alkyl groups of $R^{2b}$ may be optionally substituted by one or more hydroxyl groups;

with the proviso that the compound is other than compound number 54, 373, 496 and 585; for use as a casein kinase 1 delta (CK1δ) inhibitor in the treatment of a neurodegenerative disorder, such as tauopathies.

According to one aspect of the invention there is provided a compound of formula (IB) or a pharmaceutically acceptable salt or solvate thereof:

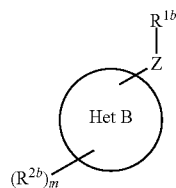

(IB)

wherein

"Het B" represents a 5 membered heterocyclic ring system containing 1 to 3 heteroatoms selected from O, N or S, wherein said ring system is fused to one or more (e.g. 1-3) further rings to form a polycyclic ring system comprising up to 4 rings;

Z represents a bond, —C($R^{7b}$)($R^{8b}$)—, (CH$_2$)$_2$, —O—, —S—, —CH$_2$—O—, —(CH$_2$)$_2$—O—, NR$^{6b}$, —N($R^{6b}$)—C($R^{7b}$)($R^{8b}$)—, N($R^{6b}$)—(CH$_2$)$_2$—, —N($R^{6b}$)—(CH$_2$)$_3$—, —CH$_2$—N($R^{6b}$)—(CH$_2$)$_2$—, —N($R^{6b}$)—CO—, —CH$_2$—NH—CO—(CH$_2$)$_2$—, —N($R^{6b}$)—CO—CH$_2$—, =N—, —C(H)(CN)—, —C(=N—NH—OOC$_{1-6}$ alkyl)-, —CH=C($R^{6b}$)—CO—, =CH—, —N=CH—, —N=C(Me)-, —C($R^{6b}$)=CH—, —NH—CO—C(=CH-heteroaryl)-, —C=C(Me)$_2$-, —CH=CH—CO—N($R^{6b}$)—, —CH=C($R^{6b}$)—NH—CO—, —CH=C($R^{6b}$)—CO—O—CH$_2$—, —CS—S—CH$_2$—, —NH—CS—NH—, —NH—CS—NH—CH$_2$—, —NH—CS—NH—(CH$_2$)$_2$—, —CH$_2$—N(CSNH$_2$)—CH$_2$—, —S—CH$_2$—, —S—(CH$_2$)$_2$—O—, SO$_2$, —NH—SO$_2$—, —CH$_2$—NH—SO$_2$—, CO, —CH$_2$—CO—, —(CH$_2$)$_2$—CO—, —O—CH$_2$—CO—, —(CH$_2$)$_2$—CO—, COO, —COO—C($R^{2b}$)CO—, —CH=C($R^{5b}$)—CONH—CH$_2$—, —CO—CH$_2$—N($R^{6b}$)—CO—, —CO—CH$_2$—C($R^{6b}$)—CH$_2$—CO—, —CO—CH$_2$—N($R^{6b}$)—CH$_2$—, —CO—NH—N=C($R^{2b}$)—, —S—CH$_2$—CO—, —S—CH$_2$—CO—N($R^{6b}$)—, —S—CH$_2$—CO—N($R^{6b}$)—CH$_2$—, —SO$_2$—N($R^{6b}$)—C($R^{7b}$)($R^{8b}$)—CONH—, —SO$_2$—N($R^{6b}$)—CH(—CH$_2$-aryl)-CONH—CH$_2$—, —CH(—S—$C_{1-6}$ alkyl)-C(Me)(OH)—, —CH$_2$—C($R^{6b}$)(OH)—, —C(OH)(CH(Me)($C_{3-8}$ cycloalkyl))—CH$_2$—, —C(OH)($R^{6b}$)—CH$_2$—, —CH(Me)-NH—CO—CH$_2$—, —CO—N($R^{6b}$)—CH$_2$—, —CO—N($R^{6b}$)—CH$_2$—CH$_2$—, —CO—N($R^{6b}$)—CH$_2$—CH$_2$—CO—NH—CH$_2$—, —CO—NH—C(—CONH$_2$)=CH—, —CO—NH—CH(—CONH$_2$)—CH$_2$—, —CH$_2$—C(H)(Me)-CH$_2$—S—, —O—CH$_2$—CO—NH—, —CH$_2$—N($R^{6b}$)—CO—CH$_2$—O—, —N($R^{6b}$)—CO—CH$_2$—O—, —C(H)(—CH$_2$-aryl)-, —C(H)(—CH$_2$-heteroaryl)-, —C(NH-aryl)-N—N=CH—, —C(NH-aryl)=N—N=CH—, —NH—N=C(-aryl)-, —NH—N=C(-aryl)-CO—, —NH—C(=N—CO—$C_{1-6}$ alkyl)-NH—(CH$_2$)$_2$—, —C(—NH-aryl)=N—N=CH—, —NH—C(—NH -aryl)=N—CONH—, —C(=CH-aryl)-CONH—CH$_2$—, —CH=C($R^{6b}$)—CONH—, —CH(—CH$_2$-aryl)-NH—CO— or —CH(OH)—, wherein said aryl or heteroaryl groups of Z may be optionally substituted by one or more halogen, $C_{1-6}$ alkyl, $C_{1-6}$ alkoxy, NO$_2$ or hydroxyl groups;

$R^{5b}$ represents hydrogen, $C_{1-6}$ alkyl or cyano;

$R^{6b}$ represents hydrogen, $C_{1-6}$ alkyl, $C_{1-6}$ alkoxy, cyano, $C_{3-8}$ cycloalkyl, —CH$_2$—$C_{3-8}$ cycloalkyl, aryl, heteroaryl, —$C_{1-6}$ alkylene-aryl, —CO-aryl, —CO-heteroaryl or —C($R^{7b}$)($R^{8b}$)-heteroaryl, wherein said aryl groups of $R^{6b}$ may be optionally substituted by one or more halogen or $C_{1-6}$ alkoxy groups;

$R^{7b}$ and $R^{8b}$ independently represent hydrogen or $C_{1-6}$ alkyl;

$R^{1b}$ represents aryl, $C_{3-8}$ cycloalkyl, monocyclic or bicyclic heterocyclyl or a monocyclic or bicyclic heteroaryl ring system, wherein $R^{1b}$ may be substituted by one or more (e.g. 1, 2 or 3) $R^{4b}$ groups;

$R^{1B}$ represents halogen, $C_{1-6}$ alkyl, $C_{1-6}$ alkenyl, $C_{1-6}$ alkynyl, $C_{3-8}$ cycloalkyl, halo$C_{1-6}$ alkyl, hydroxyl, $C_{1-6}$ alkoxy, —O—$C_{1-6}$ alkenyl, halo$C_{1-6}$ alkoxy, —COOH, —CO—$C_{1-6}$ alkyl, —COO—$C_{1-6}$ alkyl, —CONH$_2$, —CH$_2$—CONH$_2$, —NH—$C_{1-6}$ alkyl, —NH—$C_{2-6}$ alkenyl, —NH—CO—$C_{1-6}$ alkyl, —CO—NH—$C_{1-6}$ alkyl, —O—CH$_2$—CO—NH—$C_{1-6}$ alkyl, —CH$_2$—CH$_2$—CO—NH—$C_{1-6}$ alkyl, —S—$C_{1-6}$ alkyl, —SO—$C_{1-6}$ alkyl, —SO$_2$—$C_{1-6}$ alkyl, —SO$_2$—NH—$C_{1-6}$ alkyl, —S—CH$_2$—CO—C$_{2-6}$ alkenyl, —SO$_2$—OH, amino, cyano, NO$_2$, =O, —CO—NH—(CH$_2$)$_2$)—OMe, —NH—C$_{3-8}$ cycloalkyl, —CO-heterocyclyl, —CO-heteroaryl, —COO—(CH$_2$)$_2$-heterocyclyl, —OCH$_2$-aryl, —OCH$_2$-heteroaryl, —CH$_2$—O—CO-aryl, —O-aryl, —NH—CO-heteroaryl, —NH—CO—CH$_2$-aryl, aryl or heteroaryl groups, wherein said aryl, heterocyclyl or heteroaryl groups of R$^{4b}$ may be optionally substituted by one or more halogen, C$_{1-6}$ alkyl, C$_{1-6}$ alkoxy, =S or hydroxyl groups and wherein said C$_{1-6}$ alkyl or C$_{2-6}$ alkenyl groups of R$^{4b}$ may be optionally substituted by one or more hydroxyl, amino, cyano, C$_{1-6}$ alkoxy, CONH$_2$ or —COO—C$_{1-6}$ alkyl groups;

m represents an integer from 0 to 3;

R$^{2b}$ represents halogen, haloC$_{1-6}$ alkyl, C$_{1-6}$ alkyl, hydroxyl, C$_{1-6}$ alkoxy, —S— C$_{1-6}$ alkyl, —CH$_2$—S—C$_{1-6}$ alkyl, —S—C$_{2-6}$ alkynyl, amino, cyano, NO$_2$, =O, =S, —SO$_2$—C$_{1-6}$ alkyl, —CONH$_2$, —CO—C$_{1-6}$ alkyl, —COO—C$_{1-6}$ alkyl, —NH—C$_{1-6}$ alkyl, —NH—CO—C$_{1-6}$ alkyl, —NH—CO—CH=CH—CH$_2$—N(Me)$_2$, C$_{1-6}$ alkyl, —CO—NH—C$_{1-6}$ alkyl, —CO—NH—CH(Me)-COOH, —S—CH$_2$—CO—N(Et)$_2$, —NH—(CH$_2$)$_2$—OH, —NH—(CH$_2$)$_3$—OH, —NH—CH(Et) -CH$_2$—OH, —CO—NH—(CH$_2$)$_3$—OH, —CH(CH$_2$OH)$_2$ or —S—CH$_2$—CO—NH—CO—NH—C$_{1-6}$ alkyl, wherein said C$_{1-6}$ alkyl groups of R$^{2b}$ may be optionally substituted by one or more hydroxyl groups; for use as a casein kinase 1 delta (CK1δ) inhibitor in the treatment of a neurodegenerative disorder, such as tauopathies.

In one embodiment of the compound of formula (IB) "Het B" represents a 5 membered heterocyclic ring system containing 1 to 3 heteroatoms selected from O, N or S, wherein said ring system is fused to a 6 membered ring to form a bicyclic heterocyclic ring system;

Z represents a bond, —C(R$^{7b}$)(R$^{8b}$)—, —O—, —S—, CH$_2$—O—, —N(R$^{6b}$)—C(R$^{7b}$)(R$^{8b}$)—, —N(R$_{6b}$)—(CH$_2$)$_2$—, —N(R$^{6b}$)—(CH$_2$)$_3$—, —N(R$^{6b}$)—CO—, —N(R$^{6b}$)—CO—CH$_2$—, —N(R$^{7b}$)—CH=, =CH—, —N=CH—, —C(R$^{6b}$)=CH—, —C(=C(R$^{7b}$)(R$^{8b}$))—, SO$_2$, —CH$_2$—NH—SO$_2$—, CO, —O—CH$_2$—CO—, —SO$_2$—N(R$^{6b}$)—C(R$^{7b}$)(R$^{8b}$)—CONH—, —SO$_2$—N(R$^{6b}$)—CH(—CH$_2$-aryl)-CONH—CH$_2$—, —CH(—S—C$_{1-6}$ alkyl)-C(Me)(OH)—, —C(H)(R$^{6b}$)—CO—N(R$^{5b}$)—CH$_2$—, —O—CH$_2$—CO—NH—, —N(R$^{6b}$)—CO—CH$_2$—O—, —C(H)(—CH$_2$-aryl)-, —C(NH-aryl)=N—N=CH—, —NH—CO—CH$_2$—N(R$^{6b}$)—, —NH—N=C(-aryl)-, —NH—C(=N—CO—C$_{1-6}$ alkyl)-NH—(CH$_2$)$_2$—, —C(=CH-aryl)-CONH—CH$_2$— or —CH(—CH$_2$-aryl)-NH—CO— wherein said aryl or heteroaryl groups of Z may be optionally substituted by one or more halogen, C$_{1-6}$ alkyl, C$_{1-6}$ alkoxy, NO$_2$ or hydroxyl groups;

R$^{5b}$ represents hydrogen;

R$^{6b}$ represents hydrogen, methyl, C$_{1-6}$ alkoxy, —COOH, —CO-aryl, —O—CO-heteroaryl or —CO— heteroaryl, wherein said aryl groups of R$^{6b}$ may be optionally substituted by one or more halogen or C$_{1-6}$ alkoxy groups;

R$^{7b}$ and R$^{8b}$ independently represent hydrogen or C$_{1-6}$ alkyl;

R$^{1b}$ represents a monocyclic aryl or heteroaryl ring system, wherein R$^{1b}$ may be substituted by one or more (e.g. 1, 2 or 3) R$^{4b}$ groups;

R$^{4b}$ represents halogen, hydroxyl, —O—C$_{1-6}$ alkenyl, —COO—C$_{1-6}$ alkyl, —NH—C$_{1-6}$ alkyl, —SO$_2$—NH$_2$, amino, cyano, =O, —CH$_2$—CO—NH—C$_{3-8}$ cycloalkyl, —CH$_2$-aryl, —OCH$_2$-heteroaryl, —O-aryl, —NH—CO -aryl, —NH-aryl or heteroaryl groups, wherein said aryl, heterocyclyl or heteroaryl groups of R$^{4b}$ may be optionally substituted by one or more halogen, C$_{1-6}$ alkyl, C$_{1-6}$ alkoxy, =S or hydroxyl groups and wherein said C$_{1-6}$ alkyl or C$_{2-6}$ alkenyl groups of R$^{4b}$ may be optionally substituted by one or more hydroxyl, amino, cyano, C$_{1-6}$ alkoxy, CONH$_2$ or —COO—C$_{1-6}$ alkyl groups;

m represents an integer from 0 to 2; and

R$^{2b}$ represents halogen, haloC$_{1-6}$ alkyl, C$_{1-6}$ alkyl, C$_{3-8}$cycloalkyl, hydroxyl, C$_{1-6}$ alkoxy, —S—C$_{1-6}$ alkyl, amino, cyano, NO$_2$, =O, —CONH$_2$, —CO—C$_{1-6}$ alkyl, —COO—C$_{1-6}$ alkyl, C$_{1-6}$ alkyl, —CO—NH—C$_{1-6}$ alkyl or —CO—NH—CH(Me)-COOH, wherein said C$_{1-6}$ alkyl groups of R$^{2b}$ may be optionally substituted by one or more cyano or hydroxyl groups.

In one embodiment, Het B represents a 5 membered heterocyclic ring system containing 1 to 3 heteroatoms selected from O, N or S, wherein said ring system is fused to a 6 membered ring to form a bicyclic heterocyclic ring system. In a further embodiment, Het B represents benzoxazolyl, indolyl or indolizinyl.

In one embodiment, R$^{5b}$ represents hydrogen.

In one embodiment, R$^{6b}$ represents hydrogen, C$_{1-6}$ alkyl, C$_{1-6}$ alkoxy, —COOH, —CO-aryl, —O—CO-heteroaryl, —CO-heteroaryl or —C(R$^{7b}$)(R$^{8b}$)-heteroaryl, wherein said aryl groups of R$^{6b}$ may be optionally substituted by one or more halogen or C$_{1-6}$ alkoxy groups.

In one embodiment, R$^{1b}$ represents a monocyclic aryl or heteroaryl ring system, wherein R$^{1b}$ may be substituted by one or more (e.g. 1, 2 or 3) R$^{4b}$ groups. In a further embodiment, R$^{1b}$ represents a monocyclic aryl group such as phenyl optionally substituted by one or more (e.g. 1) R$^{4b}$ groups. In an alternative embodiment, R$^{1b}$ represents a monocyclic heteroaryl group such as thienyl, pyrimidinyl or pyrazolinyl optionally substituted by one or more (e.g. 1 or 2) R$^{4b}$ groups.

In one embodiment, R$^{4b}$ represents halogen, hydroxyl, —O—C$_{1-6}$ alkenyl, —COO—C$_{1-6}$ alkyl, —NH—C$_{1-6}$ alkyl, —SO$_2$—NH$_2$, amino, cyano, =O, —CH$_2$—CO—NH—C$_{3-8}$ cycloalkyl, —CH$_2$-aryl, —OCH$_2$-heteroaryl, —O-aryl, —NH—CO-aryl, —NH-aryl or heteroaryl groups, wherein said aryl, heterocyclyl or heteroaryl groups of R$^{4b}$ may be optionally substituted by one or more halogen, C$_{1-6}$ alkyl, C$_{1-6}$ alkoxy, =S or hydroxyl groups and wherein said C$_{1-6}$ alkyl or C$_{2-6}$ alkenyl groups of R$^{4b}$ may be optionally substituted by one or more hydroxyl, amino, cyano, C$_{1-6}$ alkoxy, CONH$_2$ or —COO—C$_{1-6}$ alkyl groups.

In a further embodiment, R$^{4b}$ represents halogen (e.g. fluorine), amino or heteroaryl (e.g. pyridyl).

In one embodiment, Z represents a bond, —C(R$^{7b}$)(R$^{8b}$)—, —O—, —S—, —CH$_2$—O—, —N(R$^{6b}$)—C(R$^{7b}$)(R$^{8b}$)—, —N(R$^{6b}$)—(CH$_2$)$_2$—, —N(R$^{6b}$)—(CH$_2$)$_3$—, —N(R$^{6b}$)—CO —, —N(R$^{6b}$)—CO—CH$_2$—, —N(R$^{7b}$)—CH=, =CH—, —N=CH—, —C(R$^{6b}$)=CH—, —C(=C(R$^{7b}$)(R$^{8b}$)) SO$_2$, —CH$_2$—NH—SO$_2$—, CO, —O—CH$_2$—CO—, —SO$_2$—N(R$^{6b}$)—C(R$^{7b}$)(R$^{8b}$)—CONH—, —SO$_2$—N(R$^{6b}$)—CH(—CH$_2$-aryl)-CON H—CH$_2$—, —CH(—S—C$_{1-6}$alkyl)-C(Me)(OH)—, —C(H)(R$^{6b}$)—CO—N(R$^{5b}$)—CH$_2$—, —O—CH$_2$—CO—NH—, —N(R$^{6b}$)—CO—CH$_2$—O—, —C(H)(—CH$_2$-aryl)-, —C(NH-aryl)=N—N=CH—, —NH—CO—CH$_2$—N(R$^{6b}$)—, —NH—N=C(-aryl)-, —NH—C(=N—CO—C$_{1-6}$ alkyl)-NH—(CH$_2$)$_2$—, —C(=CH-aryl)-CONH—CH$_2$— or —CH(—CH$_2$-aryl)-NH—CO— wherein said aryl or heteroaryl groups of Z may be optionally substituted by one or more halogen, C$_{1-6}$ alkyl, C$_{1-6}$ alkoxy, NO$_2$ or hydroxyl groups.

In a further embodiment, Z represents a bond or CO.

In one embodiment, m represents an integer from 0 to 2. In one embodiment, m represents 0. In an alternative embodiment, m represents 2.

In one embodiment, $R^{2b}$ represents halogen, haloC$_{1-6}$ alkyl, C$_{1-6}$ alkyl, C$_{3-8}$ cycloalkyl, hydroxyl, C$_{1-6}$ alkoxy, —S—C$_{1-6}$ alkyl, amino, cyano, NO$_2$, =O, —CONH$_2$, —CO—C$_{1-6}$ alkyl, —COO—C$_{1-6}$ alkyl, C$_{1-6}$ alkyl, —CO—NH—C$_{1-6}$ alkyl or —CO—NH—CH(Me)-COOH, wherein said C$_{1-6}$ alkyl groups of $R^{2b}$ may be optionally substituted by one or more cyano or hydroxyl groups.

In a further embodiment, $R^{2b}$ represents amino or —CONH$_2$.

In one embodiment, the compound of formula (IB) is selected from any of compounds 2-3, 26-28, 30-33, 35, 47-48, 51, 57-60, 63-64, 78, 84, 113, 123, 127-129, 145, 155-157, 171-173, 204, 206-207, 210, 225, 227, 233, 235-236, 241-242, 244, 249, 269, 285, 288, 303, 307-312, 314-316, 320, 324-325, 333, 336, 351, 357-360, 374-375, 384-391, 396, 399-402, 404-405, 407-411, 414, 424-425, 427-428, 437, 448, 456-457, 482, 484-485, 489-491, 495, 497-498, 505, 507, 516, 519, 524, 526, 553, 559-560, 568, 570, 575, 609, 615-616, 618, 626-627, 638, 653, 669, 692-694, 705, 709, 712, 716, 719, 725, 734, 738, 740, 746, 749, 753-754, 756, 758-759, 767, 770, 777, 784-785, 790, 792, 796, 800-801, 804-805, 808, 819, 821, 827-828, 831, 833, 838, 844, 847, 857-858, 869, 872, 875, 933, 952, 955, 969, 987, 990 or 999 as described herein or a pharmaceutically acceptable salt or solvate thereof.

In a further embodiment, the compound of formula (IB) is selected from any of compounds 2-3, 26-28, 30, 32-33, 47-48, 51, 59-60, 84, 113, 123, 127, 129, 145, 155, 157, 172-173, 204, 206-207, 210, 225, 233, 235-236, 241, 244, 269, 285, 288, 307-311, 315-316, 320, 324-325, 333, 336, 351, 357-360, 374-375, 385-386, 388-391, 396, 399-402, 404-405, 407-410, 414, 424, 427-428, 437, 457, 482, 490, 495, 497-498, 505, 516, 519, 553, 559-560 or 568 as described herein or a pharmaceutically acceptable salt or solvate thereof.

In a yet further embodiment, the compound of formula (IB) is selected from any of compounds 30, 314, 324-325, 391, 405, 626, 705, 753-754, 759, 770, 784, 808, 833 or 847 as described herein or a pharmaceutically acceptable salt or solvate thereof.

In a still yet further embodiment, the compound of formula (IB) is selected from any of compounds 324-325, 405, 754 or 847 as described herein or a pharmaceutically acceptable salt or solvate thereof.

In one embodiment, the compound of formula (IB) is selected from any of compounds 30, 288, 314, 324-325, 336, 374, 391, 405, 615-616, 626, 705, 740, 753-754, 756, 759, 770, 784, 808, 819, 833, 844, 847, 869, 872, 875, 933, 952, 955, 969, 987, 990 and 999 as described herein or a pharmaceutically acceptable salt or solvate thereof. The compounds of this embodiment were tested in the CK1δ inhibition assay as described herein and exhibited inhibition of greater than 5%.

In a further embodiment, the compound of formula (IB) is selected from any of compounds 324-325, 405, 754, 847, 952, 987, 990 and 999 as described herein or a pharmaceutically acceptable salt or solvate thereof. The compounds of this embodiment were tested in the CK1δ inhibition assay as described herein and exhibited inhibition of greater than 50%.

In a yet further embodiment, the compound of formula (IB) is selected from any one of compounds:

5-(1,3-benzoxazol-2-yl)-4-(pyridin-4-yl)pyrimidin-2-amine (Compound 324);

2-amino-3-[(thiophen-2-yl)carbonyl]indolizine-1-carboxamide (Compound 847);

2-[3-(pyridin-4-yl)-1H-pyrazol-4-yl]-1,3-benzoxazole (Compound 952);

2-amino-3-[(4-fluorophenyl)carbonyl]indolizine-1-carboxamide (Compound 987);

2-amino-3-benzoylindolizine-1-carboxamide (Compound 990); and 2-amino-1-[(4-fluorophenyl)carbonyl]-1H-indole-3-carboxamide (Compound 999);

or a pharmaceutically acceptable salt or solvate thereof.

In a yet further embodiment, the compound of formula (IB) is selected from any of compounds 324, 952, 987, 990 and 999 as described herein or a pharmaceutically acceptable salt or solvate thereof. The compounds of this embodiment were tested in the CK1δ inhibition assay as described herein and exhibited inhibition of greater than 90%.

In a still yet further embodiment, the compound of formula (IB) is selected from any of compounds 324, 952, 987 and 999 as described herein or a pharmaceutically acceptable salt or solvate thereof. The compounds of this embodiment were tested in a range of kinase inhibition assays and not only exhibited inhibition of greater than 90% in the CK1δ inhibition assay as described herein, but also demonstrated significant and selective inhibition for CK1δ when compared with other kinases.

For example, compound number 324 (5-(1,3-benzoxazol-2-yl)-4-(pyridin-4-yl)pyrimidin-2-amine) demonstrated selectivity for CK1δ over ABL2/ARG, ALK4/ACVR1B, ALK5/TGFBR1, CDK5/p25, CK1a1, CK1g1, CK1g3, CLK2, c-SRC, EGFR, EPHA2, FGFR1, GSK3b, HGK/MAP4K4, JNK2, KDR/VEGFR2, LCK, MSK1/RPS6KA5, PDK1/PDPK1, PIM3, PKA, PKCa, PKCb2, RIPK2, ROCK1, TNIK and YES/YES1 each of which were inhibited at levels lower than 40%.

For example, compound number 952 (2-[3-(pyridin-4-yl)-1H-pyrazol-4-yl]-1,3-benzoxazole) demonstrated selectivity for CK1δ over ABL2/ARG, ALK4/ACVR1B, ALK5/TGFBR1, CDK5/p25, CK1g1, CK1g2, CK1g3, c-SRC, EGFR, EPHA2, FGFR1, KDR/VEGFR2, LCK, MSK1/RPSKA5, PDK1/PDPK1, PIM3, PKA, PKCa, PKCb2, ROCK1 and YES/YES1 each of which were inhibited at levels lower than 40%.

For example, compound number 987 (2-amino-3-[(4-fluorophenyl)carbonyl]indolizine-1-carboxamide) demonstrated selectivity for CK1δ over ABL2/ARG, CDK5/p25, CK1g1, CK1g2, CK1g3, CLK2, c-SRC, FGFR1, GSK3b, HGK/MAP4K4, JNK2, KDR/VEGFR2, LCK, MSK1/RPS6KA5, PDK1/PDPK1, PIM3, PKCa, PKCb2, ROCK1 and TNIK each of which were inhibited at levels lower than 40%.

For example, compound number 999 (2-amino-1-[(4-fluorophenyl)carbonyl]-1H-indole-3-carboxamide) demonstrated selectivity for CK1δ over ABL2/ARG, CDK5/p25, CK1g1, CK1g2, CLK2, c-SRC, FGFR1, GSK3b, HGK/MAP4K4, KDR/VEGFR2, LCK, MSK1/RPS6KA5, PDK1/PDPK1, PIM3, PKCa, PKCb2 and ROCK1 each of which were inhibited at levels lower than 40%.

In a still yet further embodiment, the compound of formula (IB) is selected from any of compounds 324 and 987 as described herein or a pharmaceutically acceptable salt or solvate thereof. The compounds of this embodiment have been demonstrated to have a protective effect on cell viability as can be seen in the data presented herein and in particular within FIGS. 1 and 2. The compounds of this embodiment have also been demonstrated to inhibit phosphorylation of two different amino acid residues within Tau proteins (i.e. Ser 396 and Thr 391) as shown in FIGS. 4 and 5.

In a still yet further embodiment, the compound of formula (IB) is compound 324 as described herein or a pharmaceutically acceptable salt or solvate thereof. The compound of this embodiment has been demonstrated to have a protective effect on cell viability in a dose dependent manner as can be seen in the data presented herein and in particular within FIG. 1. The compound of this embodiment has also been demonstrated to inhibit phosphorylation of two different amino acid residues within Tau proteins (i.e. Ser 396 and Thr 391) as shown in FIGS. 4A and 5.

Figure 1:
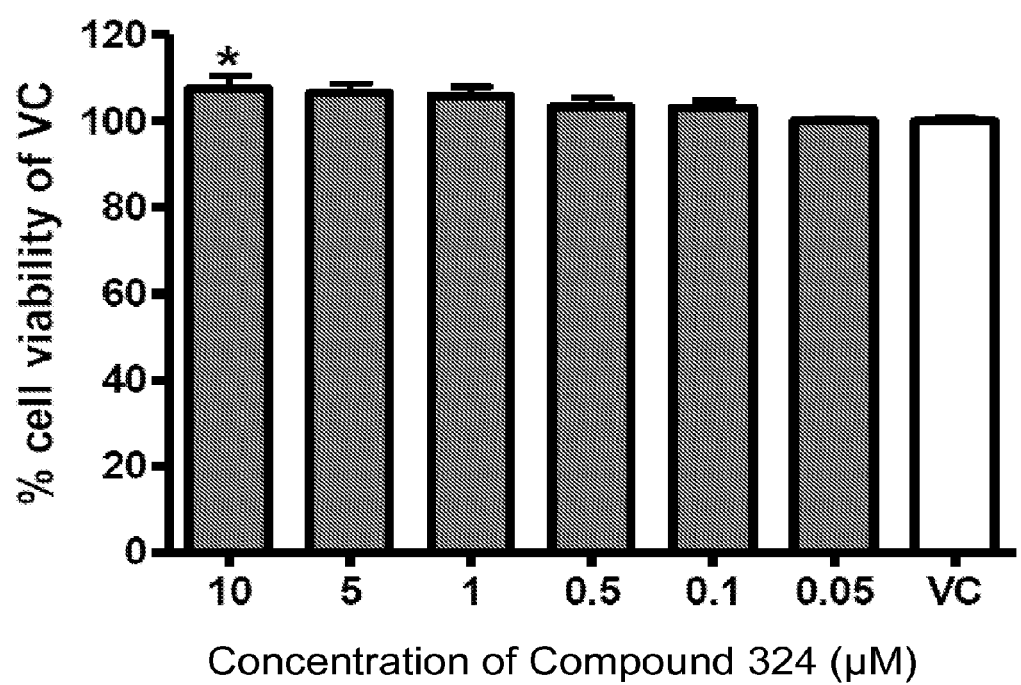
FIG. 1 shows the effect of Compound 324 on the cell viability of SH-SY5Y-TMHT cells.

In the present context, the term "pharmaceutically acceptable salt" is intended to indicate salts which are not harmful to the patient. Such salts include pharmaceutically acceptable acid addition salts, pharmaceutically acceptable metal salts and pharmaceutically acceptable alkaline addition salts. Acid addition salts include salts of inorganic acids as well as organic acids.

Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Representative examples of alkaline salts include, for example, sodium, potassium, lithium, calcium, magnesium or ammonium or organic bases such as, for example, methylamine, ethylamine, propylamine, trimethylamine, diethylamine, triethylamine, N,N-dimethylethanolamine, tris(hydroxymethyl)aminomethane, ethanolamine, pyridine, piperidine, piperazine, picoline, dicyclohexylamine, morpholine, benzylamine, procaine, lysine, arginine, histidine, N-methylglucamine.

According to the invention, the compounds of formula (IB) can be in racemic forms, as well as in the form of pure enantiomers or non racemic (scalemic) mixture of enantiomers, including when the compounds of formula (IB) have more than one stereogenic centre. In case the compounds of formula (IB) have unsaturated carbon carbon double bonds, both the cis (Z) and trans (E) isomers and their mixtures belong to the invention.

References herein to "halogen" means a fluorine, chlorine, bromine or iodine atom.

References herein to "$C_{1-6}$ alkyl" means any linear, branched hydrocarbon groups having 1 to 6 carbon atoms, or cyclic hydrocarbon groups having 3 to 6 carbon atoms. Representative examples of such alkyl groups include methyl, ethyl, n-propyl, isopropyl, n-butyl, isobutyl and t-butyl, n-pentyl, isopentyl, neopentyl, cyclopropyl, cyclobutyl, cyclopentyl and cyclohexyl. References to "halo$C_{1-6}$alkyl" mean a $C_{1-6}$ alkyl group substituted by one or more halogen atoms as herein defined.

References herein to "$C_{1-6}$ alkylene" means a saturated divalent hydrocarbon chain having the specified number of member atoms. For example, $C_{1-6}$ alkylene refers to a bond or an alkylene group having from 1 to 6 member atoms. Alkylene groups may be straight or branched. Representative branched alkylene groups have one or two branches. Alkylene includes methylene, ethylene, propylene (n-propylene and isopropylene) and butylene (n-butylene, isobutylene, and t-butylene).

References herein to "$C_{2-6}$ alkenyl" means any linear, branched hydrocarbon groups of 2 to 6 carbon atoms, or cyclic hydrocarbon group having 3 to 6 carbon atoms having at least one double bond. Representative examples of such alkenyl groups include ethenyl, propenyl, butenyl and cyclohexenyl.

References herein to "$C_{2-6}$ alkynyl" means any linear, or branched hydrocarbon groups of 2 to 6 carbon atoms, having at least one triple bond. Representative examples of such alkynyl groups include ethynyl, propargyl and butynyl.

References herein to "$C_{1-6}$ alkoxy" means an —O—$C_{1-6}$ alkyl group wherein $C_{1-6}$ alkyl is as defined herein. Examples of such groups include methoxy, ethoxy, propoxy, butoxy, pentoxy or hexoxy and the like.

References herein to "$C_{3-8}$ cycloalkyl" means a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

References herein to "aryl" means a $C_{6-12}$ monocyclic or bicyclic hydrocarbon ring wherein at least one ring is aromatic. Examples of such groups include phenyl, indyl or naphthyl and the like.

References herein to "heteroatom" means a nitrogen, sulphur, or oxygen atom.

References herein to "heterocyclyl" means a saturated or unsaturated non-aromatic ring containing from 1 to 4 heteroatoms as member atoms in the ring. Heterocyclyl groups containing more than one heteroatom may contain different heteroatoms. Heterocyclyl groups may be optionally substituted with one or more substituents as defined herein. Heterocyclyl groups are monocyclic ring systems or fused bicyclic or polycyclic ring systems or bicyclic structures known as heterocyclic "spiro" ring systems. In certain embodiments, heterocyclyl is saturated. In other embodiments, heterocyclyl is unsaturated and non-aromatic. Non-limiting examples of monocyclic heterocyclyl ring systems include pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, and azetidinyl.

References herein to "heteroaryl" means an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused bicyclic or polycyclic ring systems. Monocyclic heteroaryl rings have 5 or 6 member atoms. Bicyclic heteroaryl rings have from 7 to 11 member atoms. Bicyclic heteroaryl rings include those rings wherein phenyl and a monocyclic heterocyclyl ring are attached forming a fused bicyclic ring system, and those rings wherein a monocyclic heteroaryl ring and a monocyclic cycloalkyl, cycloalkenyl, heterocyclyl, or heteroaryl ring are attached forming a fused bicyclic ring system. Non-limiting examples of heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benopyranyl, benzoxazolyl, benzofuranyl, isobenzofuranyl, benzothiazolyl, benzothienyl, furopyridinyl, and napthyridinyl.

References herein to "heterocyclic ring system" mean either a heterocyclyl ring system or a heteroaryl ring system as hereinbefore defined.

Representative compounds of formula (IB) include the compounds as set forth below:

| Compound Number | Structure |
|---|---|
| 2 | |
| 3 | |
| 26 | |
| 27 | |
| 28 | 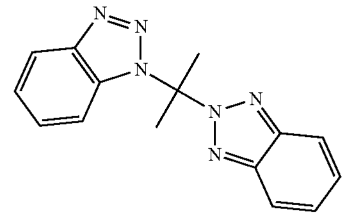 [SMILES: CC(C)(n1nc2ccccc2n1)n1nnc2ccccc21] |
| 30 | 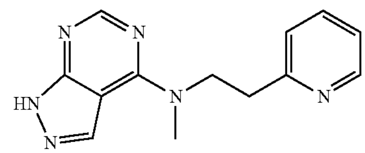 [SMILES: CN(CCc1ccccn1)c1ncnc2[nH]ncc12] |
| 31 | 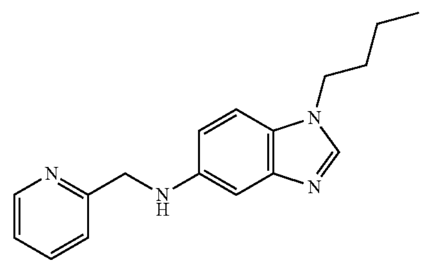 [SMILES: CCCCn1cnc2cc(NCc3ccccn3)ccc21] |
| 32 | 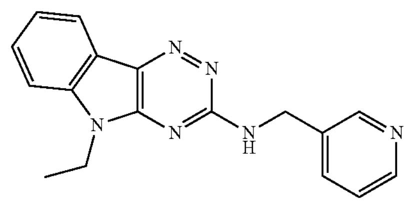 [SMILES: CCn1c2ccccc2c2nnc(NCc3cccnc3)nc21] |
| 33 | 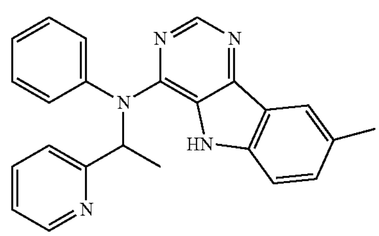 [SMILES: Cc1ccc2[nH]c3c(N(c4ccccc4)C(C)c4ccccn4)ncnc3c2c1] |
| 35 | 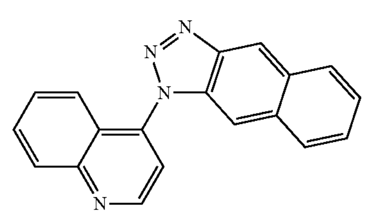 [SMILES: c1ccc2cc3c(cc2c1)nnn3-c1ccnc2ccccc12] |
| 47 | 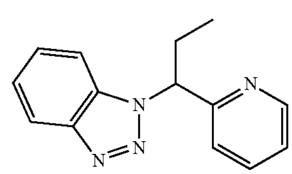 [SMILES: CCC(c1ccccn1)n1nnc2ccccc21] |

-continued
| Compound Number | Structure |
|---|---|
| 48 | 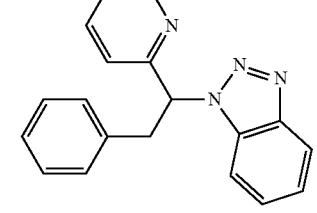 |
| 51 | 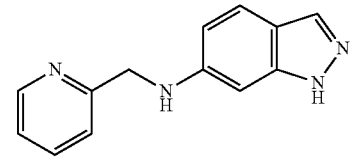 [SMILES: c1ccc(CNc2ccc3cn[nH]c3c2)nc1] |
| 54 | 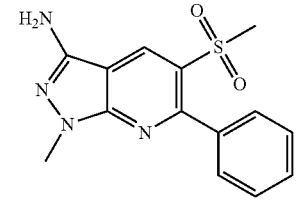 [SMILES: Cn1nc(N)c2cc(S(C)(=O)=O)c(-c3ccccc3)nc21] |
| 57 | 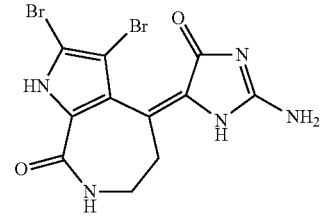 [SMILES: NC1=NC(=O)/C(=C2/CCNC(=O)c3[nH]c(Br)c(Br)c32)N1] |
| 58 | 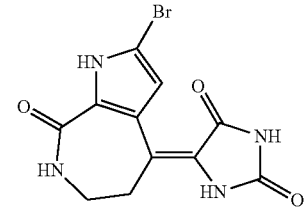 [SMILES: O=C1NC(=O)/C(=C2/CCNC(=O)c3[nH]c(Br)cc32)N1] |
| 59 | 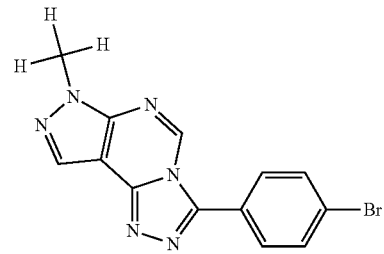 [SMILES: Cn1ncc2c1ncn1c(-c3ccc(Br)cc3)nnc21] |
-continued
| Compound Number | Structure |
|---|---|
| 60 | 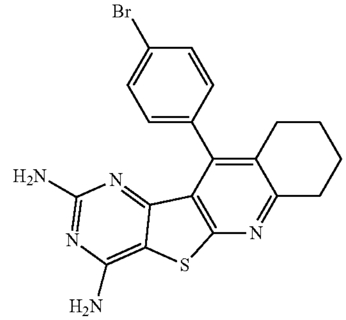 [SMILES: Nc1nc(N)c2sc3nc4c(c(-c5ccc(Br)cc5)c3c2n1)CCCC4] |
| 63 | 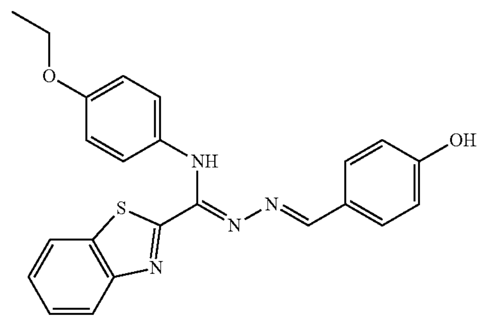 [SMILES: CCOc1ccc(N/C(=N\N=C\c2ccc(O)cc2)c2nc3ccccc3s2)cc1] |
| 64 | 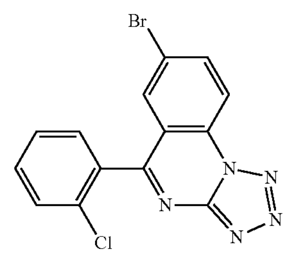 [SMILES: Clc1ccccc1-c1nc2nnnn2c2ccc(Br)cc12] |
| 78 | 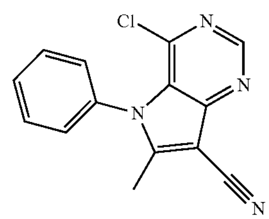 [SMILES: Cc1c(C#N)c2ncnc(Cl)c2n1-c1ccccc1] |
| 84 | 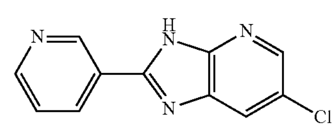 [SMILES: Clc1cnc2[nH]c(-c3cccnc3)nc2c1] |
| 113 | 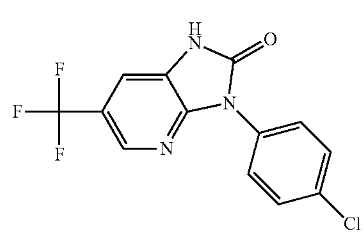 [SMILES: O=c1[nH]c2cc(C(F)(F)F)cnc2n1-c1ccc(Cl)cc1] |

-continued

| Compound Number | Structure |
|---|---|
| 123 | (structure) |
| 127 | (structure) |
| 128 | (structure) |
| 129 | (structure) |
| 145 | (structure) |
| 155 | (structure) |
| 156 | (structure) |
| 157 | (structure) |
| 171 | (structure) |
| 172 | (structure) |
| 173 | (structure) |

| Compound Number | Structure |
|---|---|
| 204 | 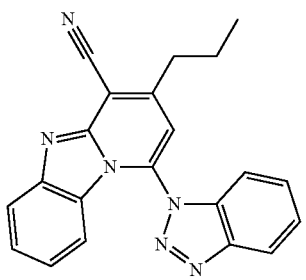 [SMILES: CCCc1cc(-n2nnc3ccccc32)n2c(nc3ccccc32)c1C#N] |
| 206 | 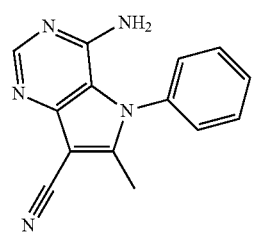 [SMILES: Cc1c(C#N)c2ncnc(N)c2n1-c1ccccc1] |
| 207 | 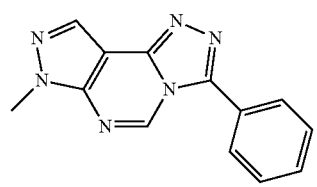 [SMILES: Cn1ncc2c1ncn1c(-c3ccccc3)nnc21] |
| 210 | 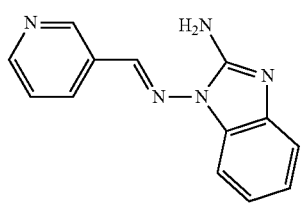 [SMILES: Nc1nc2ccccc2n1/N=C/c1cccnc1] |
| 225 | 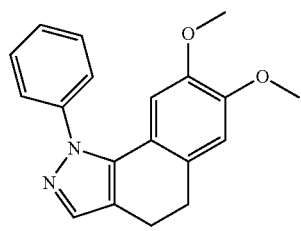 [SMILES: COc1cc2c(cc1OC)-c1c(cnn1-c1ccccc1)CC2] |
| 227 | 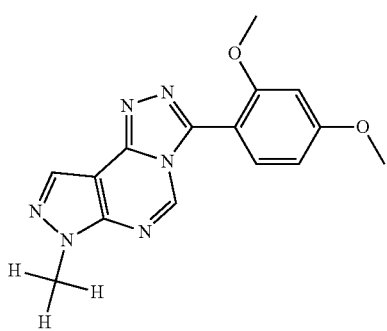 [SMILES: COc1ccc(-c2nnc3c4cnn(C)c4ncn23)c(OC)c1] |
| Compound Number | Structure |
|---|---|
| 233 | 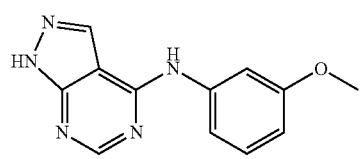 [SMILES: COc1cccc(Nc2ncnc3[nH]ncc23)c1] |
| 235 | 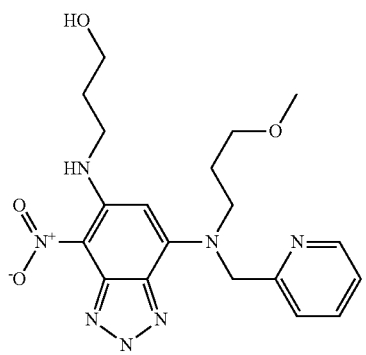 |
| 236 | 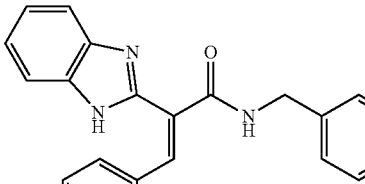 |
| 241 | 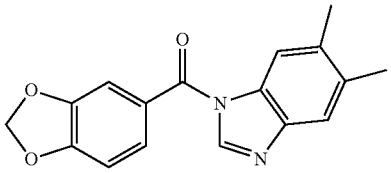 [SMILES: Cc1cc2ncn(C(=O)c3ccc4c(c3)OCO4)c2cc1C] |
| 242 | 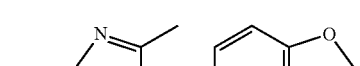 |
| 244 | 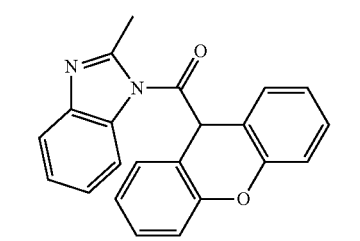 [SMILES: Cc1nc2ccccc2n1C(=O)C1c2ccccc2Oc2ccccc21] |

| Compound Number | Structure |
|---|---|
| 249 | |
| 269 | |
| 285 | |
| 288 | |
| 303 | |
| 307 | |
| 308 | 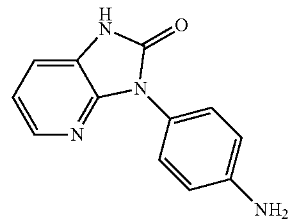 [SMILES: Nc1ccc(-n2c(=O)[nH]c3cccnc32)cc1] |
| 309 | 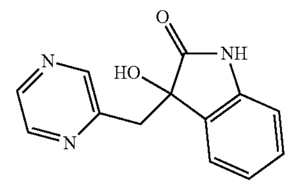 [SMILES: O=C1Nc2ccccc2C1(O)Cc1cnccn1] |
| 310 | 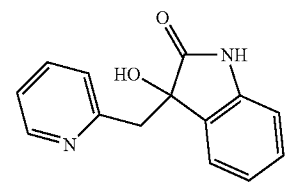 [SMILES: O=C1Nc2ccccc2C1(O)Cc1ccccn1] |
| 311 | 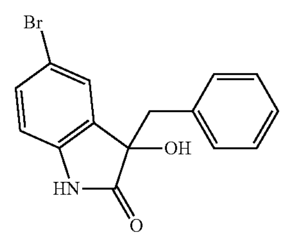 [SMILES: O=C1Nc2ccc(Br)cc2C1(O)Cc1ccccc1] |
| 312 | 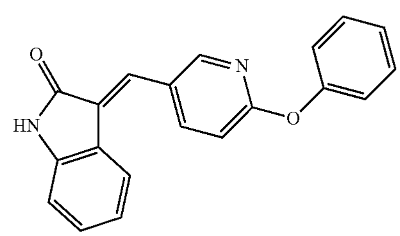 [SMILES: O=C1Nc2ccccc2/C1=C\c1ccc(Oc2ccccc2)nc1] |
| 314 | 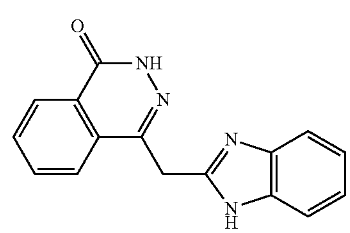 [SMILES: O=c1[nH]nc(Cc2nc3ccccc3[nH]2)c2ccccc12] |
| 315 | 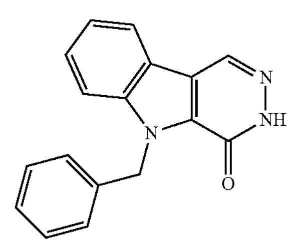 [SMILES: O=c1[nH]ncc2c3ccccc3n(Cc3ccccc3)c12] |

| Compound Number | Structure |
|---|---|
| 316 | 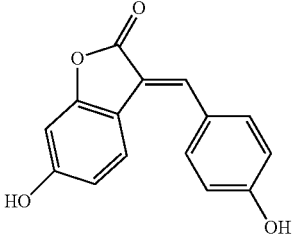 [SMILES: O=C1Oc2cc(O)ccc2/C1=C\c1ccc(O)cc1] |
| 320 | 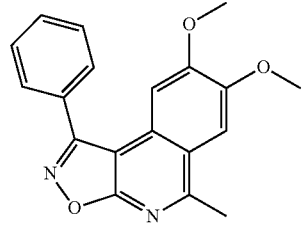 [SMILES: COc1cc2c(C)nc3onc(-c4ccccc4)c3c2cc1OC] |
| 324 | 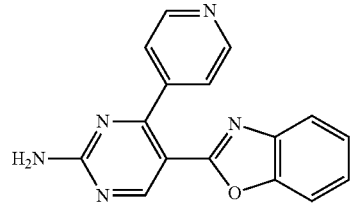 [SMILES: Nc1ncc(-c2nc3ccccc3o2)c(-c2ccncc2)n1] |
| 325 | 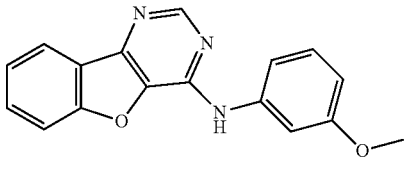 [SMILES: COc1cccc(Nc2ncnc3c2oc2ccccc23)c1] |
| 333 | 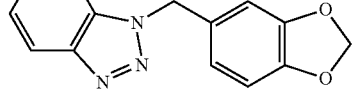 |
| 336 | 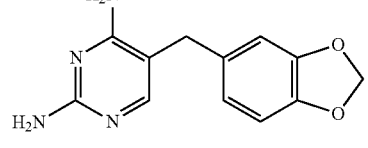 |
| 351 | 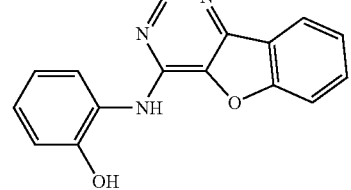 |
| 357 | 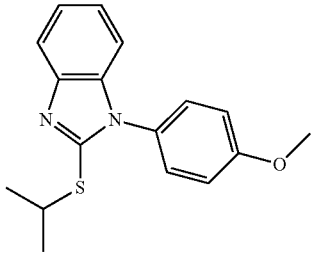 [SMILES: COc1ccc(-n2c(SC(C)C)nc3ccccc32)cc1] |
| 358 | 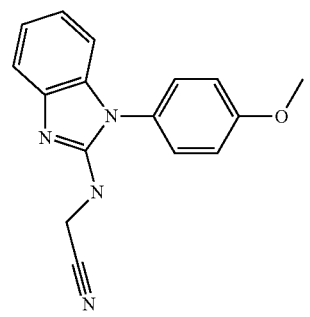 [SMILES: COc1ccc(-n2c(NCC#N)nc3ccccc32)cc1] |
| 359 | 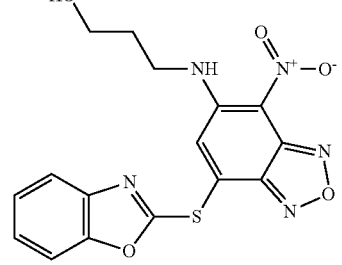 |
| 360 | 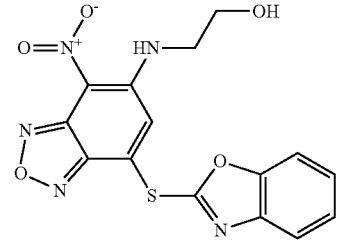 [SMILES: O=[N+]([O-])c1c(NCCO)cc(Sc2nc3ccccc3o2)c2nonc12] |
| 373 | 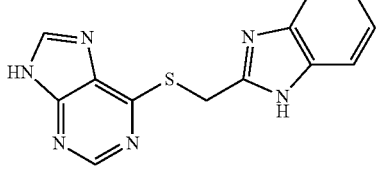 |
| 374 | 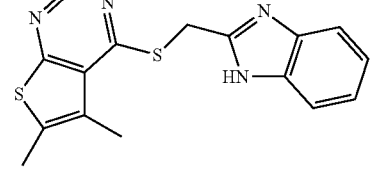 |

| Compound Number | Structure |
|---|---|
| 375 | (5-ethylthieno[2,3-d]pyrimidin-4-yl)thio-CH2-(1H-benzimidazol-2-yl) |
| 384 | benzo[1,2,5]thiadiazol-4-yl-SO2-N(CH3)-CH2-C(=O)-NH-(thiazol-2-yl) |
| 390 | benzo[1,2,5]thiadiazol-4-yl-SO2-NH-CH2-C(=O)-NH-(4-methylthiazol-2-yl) |
| 391 | thieno[3,2-d]pyrimidin-4-yl-O-CH2-C(=O)-NH-(3-sulfamoylphenyl) |
| 396 | 3-(pyridin-4-yl)-6-isobutyl-[1,2,4]triazolo[3,4-b][1,3,4]thiadiazole |
| 399 | N-(3,4-dimethoxyphenyl)-N-(thiophen-2-ylmethyl)-5,6,7,8-tetrahydrobenzo[4,5]thieno[2,3-d]pyrimidin-4-amine |
| 400 | N-(2,3-dihydrobenzo[b][1,4]dioxin-6-yl)-5,6-dimethylthieno[2,3-d]pyrimidin-4-amine |

| Compound Number | Structure |
|---|---|
| 385 | benzo[1,2,5]thiadiazol-4-yl-SO2-NH-CH(iPr)-C(=O)-NH-(4-methylthiazol-2-yl) |
| 386 | benzo[1,2,5]thiadiazol-4-yl-SO2-NH-CH(iPr)-C(=O)-NH-(thiazol-2-yl) |
| 387 | benzo[1,2,5]thiadiazol-4-yl-SO2-NH-CH(CH2Ph)-C(=O)-NH-CH2-(pyridin-2-yl) |
| 388 | benzo[1,2,5]thiadiazol-4-yl-SO2-NH-CH(CH2Ph)-C(=O)-NH-CH2-Ph |
| 389 | benzo[1,2,5]thiadiazol-4-yl-SO2-NH-CH(CH2Ph)-C(=O)-NH-CH2-(thiophen-2-yl) |

| Compound Number | Structure |
|---|---|
| 401 | 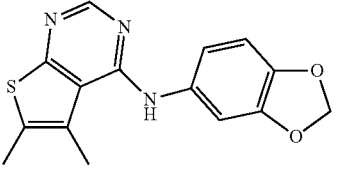 [SMILES: Cc1sc2ncnc(Nc3ccc4c(c3)OCO4)c2c1C] |
| 402 | 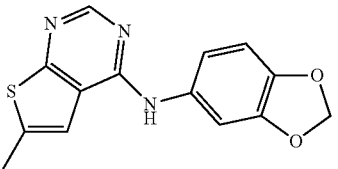 [SMILES: Cc1cc2c(Nc3ccc4c(c3)OCO4)ncnc2s1] |
| 404 | 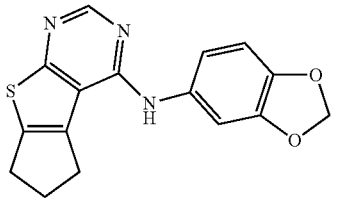 [SMILES: c1nc(Nc2ccc3c(c2)OCO3)c2c3c(sc2n1)CCC3] |
| 405 | 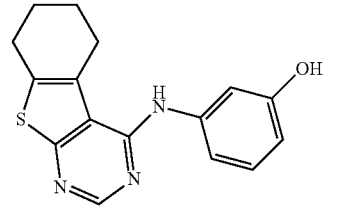 [SMILES: Oc1cccc(Nc2ncnc3sc4c(c23)CCCC4)c1] |
| 407 | 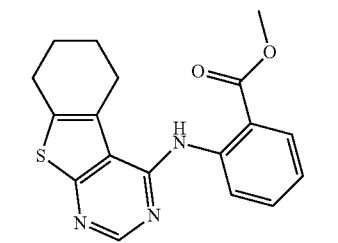 [SMILES: COC(=O)c1ccccc1Nc1ncnc2sc3c(c12)CCCC3] |
| 408 | 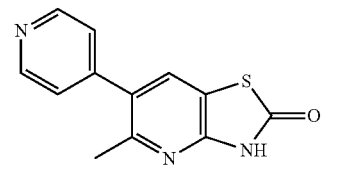 [SMILES: Cc1nc2[nH]c(=O)sc2cc1-c1ccncc1] |
| 409 | 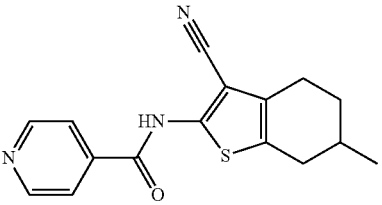 [SMILES: CC1CCc2c(sc(NC(=O)c3ccncc3)c2C#N)C1] |
| 410 | 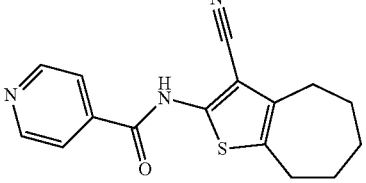 |
| 411 | 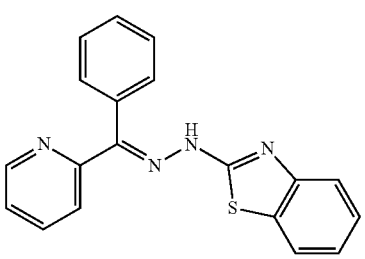 [SMILES: c1ccc(/C(=N\Nc2nc3ccccc3s2)c2ccccn2)cc1] |
| 414 | 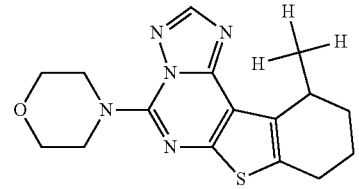 [SMILES: CC1CCCc2sc3nc(N4CCOCC4)n4ncnc4c3c21] |
| 424 | 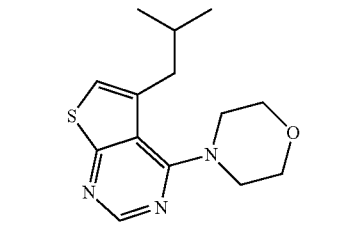 [SMILES: CC(C)Cc1csc2ncnc(N3CCOCC3)c12] |
| 425 | 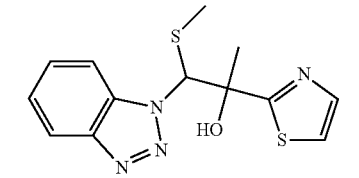 [SMILES: CSC(n1nnc2ccccc21)C(C)(O)c1nccs1] |
| 427 | 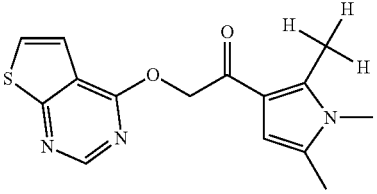 [SMILES: Cc1cc(C(=O)COc2ncnc3sccc23)c(C)n1C] |
| 428 | 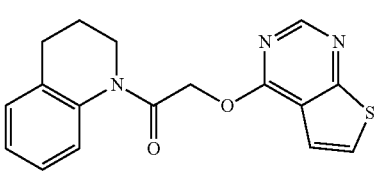 [SMILES: O=C(COc1ncnc2sccc12)N1CCCc2ccccc21] |

-continued
| Compound Number | Structure |
|---|---|
| 437 | 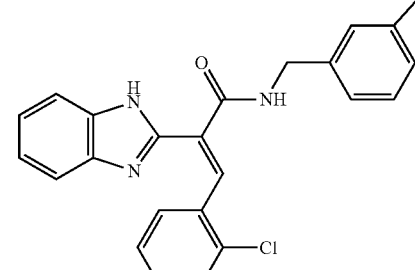 |
| 448 | 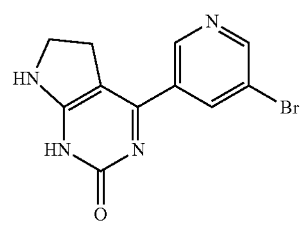 [SMILES: O=c1nc(-c2cncc(Br)c2)c2c([nH]1)NCC2] |
| 456 | 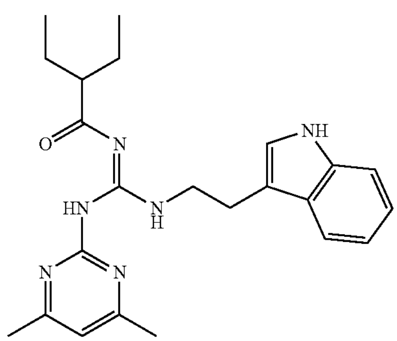 [SMILES: CCC(CC)C(=O)/N=C(/NCCc1c[nH]c2ccccc12)Nc1nc(C)cc(C)n1] |
| 457 | 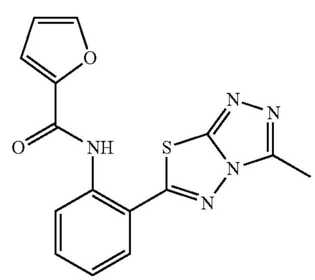 [SMILES: Cc1nnc2sc(-c3ccccc3NC(=O)c3ccco3)nn12] |
| 458 | 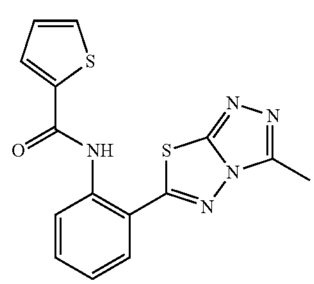 |
| 482 | 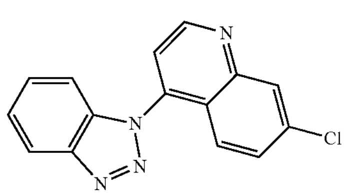 [SMILES: Clc1ccc2c(-n3nnc4ccccc43)ccnc2c1] |
-continued
| Compound Number | Structure |
|---|---|
| 484 | 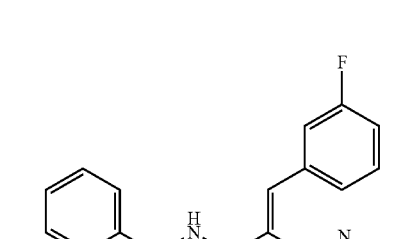 |
| 485 | 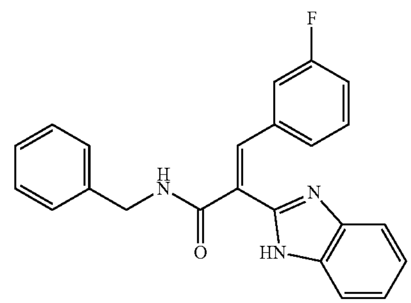 [SMILES: O=C(NCc1ccccc1)/C(=C/c1cccc(F)c1)c1nc2ccccc2[nH]1] |
| 489 | 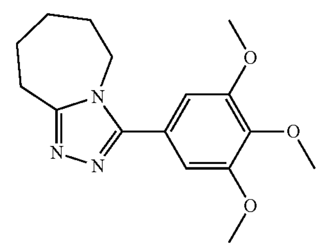 [SMILES: COc1cc(-c2nnc3n2CCCCC3)cc(OC)c1OC] |
| 490 | 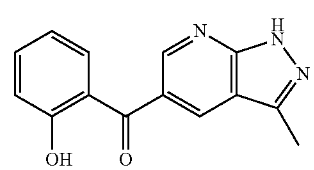 [SMILES: Cc1n[nH]c2ncc(C(=O)c3ccccc3O)cc12] |
| 491 | 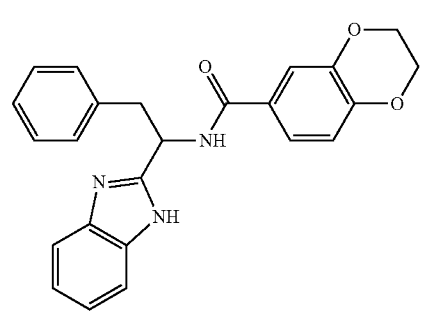 [SMILES: O=C(NC(Cc1ccccc1)c1nc2ccccc2[nH]1)c1ccc2c(c1)OCCO2] |

| Compound Number | Structure |
|---|---|
| 495 | 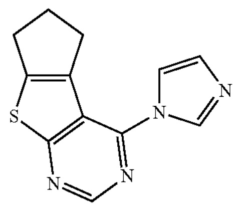 [SMILES: c1cn(-c2ncnc3sc4c(c23)CCC4)cn1] |
| 496 | 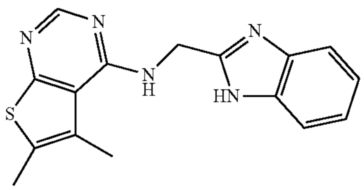 [SMILES: Cc1sc2ncnc(NCc3nc4ccccc4[nH]3)c2c1C] |
| 497 | 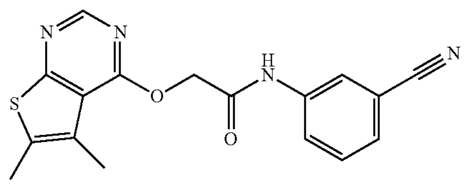 [SMILES: Cc1sc2ncnc(OCC(=O)Nc3cccc(C#N)c3)c2c1C] |
| 498 | 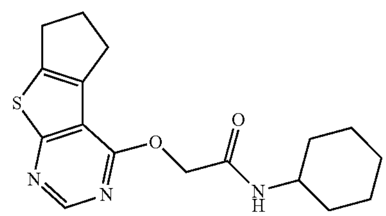 [SMILES: O=C(COc1ncnc2sc3c(c12)CCC3)NC1CCCCC1] |
| 505 | 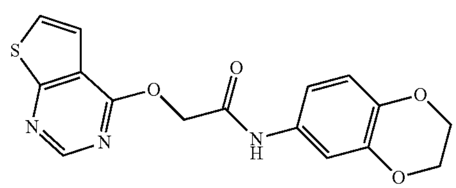 [SMILES: O=C(COc1ncnc2sccc12)Nc1ccc2c(c1)OCCO2] |
| 507 | 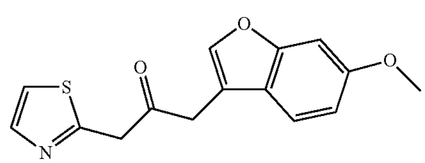 [SMILES: COc1ccc2c(CC(=O)Cc3nccs3)coc2c1] |
| 516 | 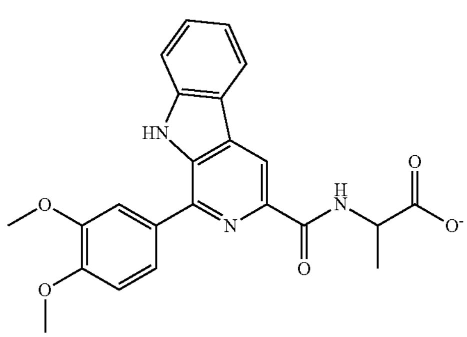 [SMILES: COc1ccc(-c2nc(C(=O)NC(C)C(=O)[O-])cc3c2[nH]c2ccccc23)cc1OC] |
| 519 | |
| 524 | |
| 526 | |
| 553 | |
| 559 | |
| 560 | |

| Compound Number | Structure |
|---|---|
| 568 | 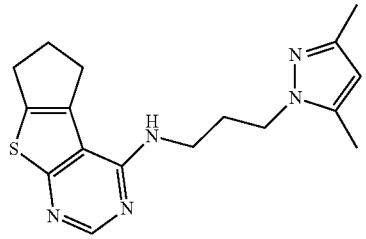 [SMILES: Cc1cc(C)n(CCCNc2ncnc3sc4c(c23)CCC4)n1] |
| 570 | 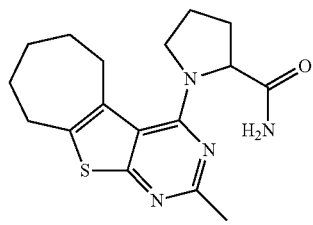 [SMILES: Cc1nc(N2CCCC2C(N)=O)c2c3c(sc2n1)CCCCC3] |
| 575 | 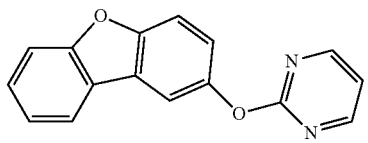 [SMILES: c1cnc(Oc2ccc3oc4ccccc4c3c2)nc1] |
| 585 | 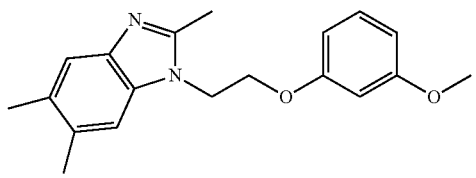 |
| 590 | 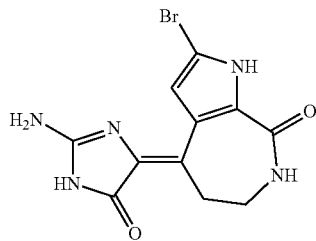 [SMILES: NC1=N/C(=C2/CCNC(=O)c3[nH]c(Br)cc32)C(=O)N1] |
| 594 | 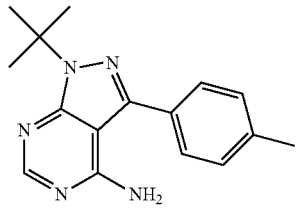 [SMILES: Cc1ccc(-c2nn(C(C)(C)C)c3ncnc(N)c23)cc1] |
| 596 | 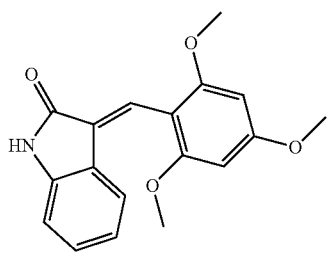 [SMILES: COc1cc(OC)c(/C=C2/C(=O)Nc3ccccc32)c(OC)c1] |
| Compound Number | Structure |
|---|---|
| 597 | 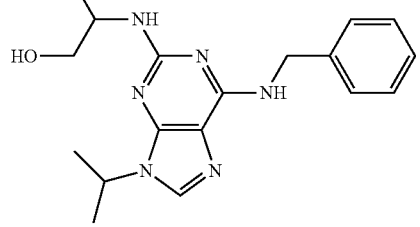 |
| 601 | 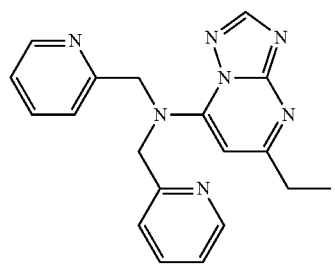 [SMILES: CCc1cc(N(Cc2ccccn2)Cc2ccccn2)n2ncnc2n1] |
| 602 | 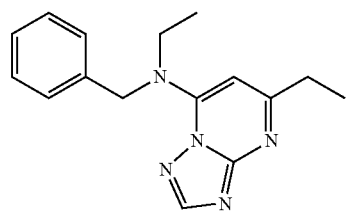 [SMILES: CCc1cc(N(CC)Cc2ccccc2)n2ncnc2n1] |
| 609 | 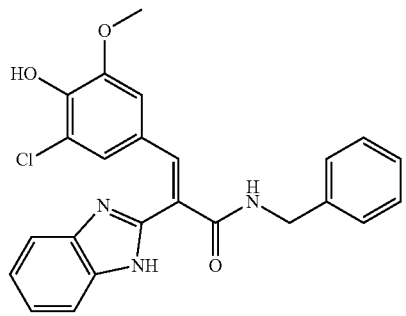 [SMILES: COc1cc(/C=C(/C(=O)NCc2ccccc2)c2nc3ccccc3[nH]2)cc(Cl)c1O] |
| 615 | 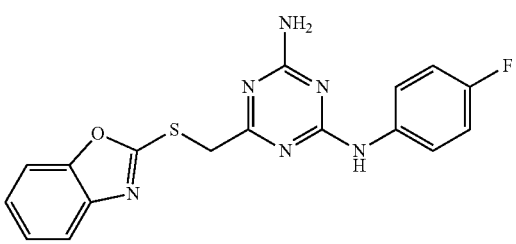 [SMILES: Nc1nc(CSc2nc3ccccc3o2)nc(Nc2ccc(F)cc2)n1] |

| Compound Number | Structure |
|---|---|
| 616 | 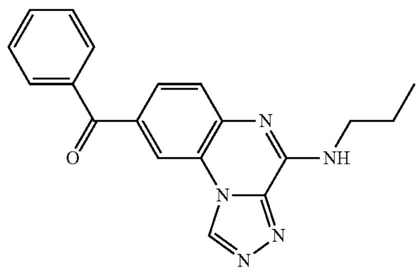 [SMILES: CCCNc1nc2ccc(C(=O)c3ccccc3)cc2n2cnnc12] |
| 618 | 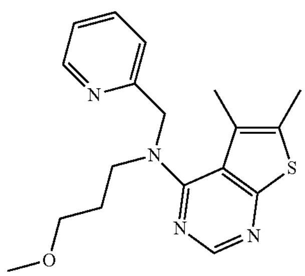 |
| 626 | 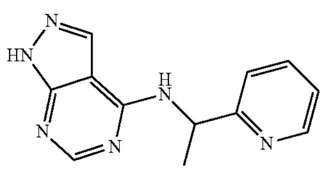 [SMILES: CC(Nc1ncnc2[nH]ncc12)c1ccccn1] |
| 627 | 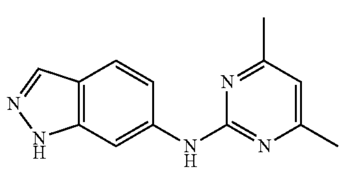 [SMILES: Cc1cc(C)nc(Nc2ccc3cn[nH]c3c2)n1] |
| 638 | 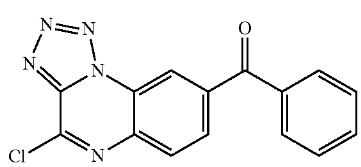 [SMILES: O=C(c1ccccc1)c1ccc2nc(Cl)c3nnnn3c2c1] |
| 649 | 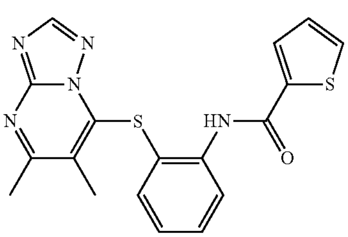 [SMILES: Cc1nc2ncnn2c(Sc2ccccc2NC(=O)c2cccs2)c1C] |
| 653 | 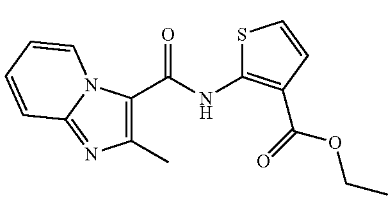 [SMILES: CCOC(=O)c1ccsc1NC(=O)c1c(C)nc2ccccn12] |
| 669 | |
| 692 | |
| 693 | |
| 694 | |
| 703 | |
| 705 | |
| 709 | |

-continued
| Compound Number | Structure |
|---|---|
| 712 | 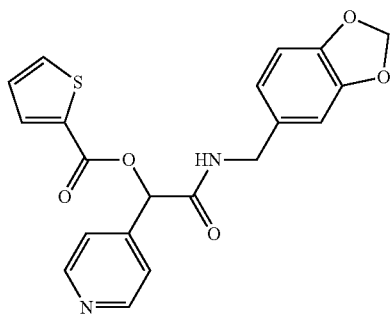 [SMILES: O=C(OC(C(=O)NCc1ccc2c(c1)OCO2)c1ccncc1)c1cccs1] |
| 716 | 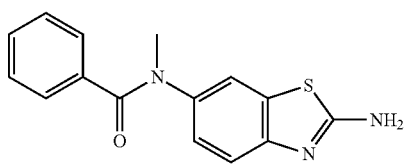 [SMILES: CN(C(=O)c1ccccc1)c1ccc2nc(N)sc2c1] |
| 719 | 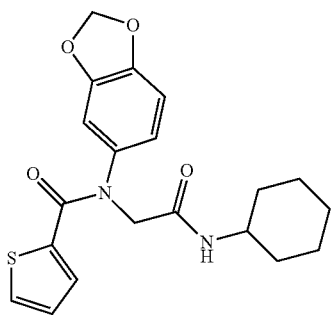 [SMILES: O=C(CN(C(=O)c1cccs1)c1ccc2c(c1)OCO2)NC1CCCCC1] |
| 725 | 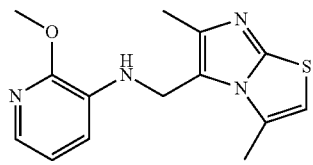 [SMILES: COc1ncccc1NCc1c(C)nc2scc(C)n12] |
| 734 | 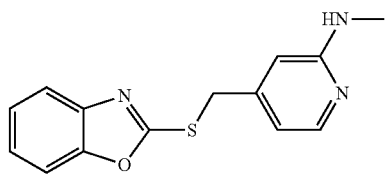 [SMILES: CNc1cc(CSc2nc3ccccc3o2)ccn1] |
| 738 | 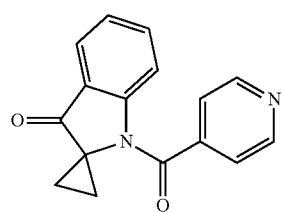 [SMILES: O=C(c1ccncc1)N1c2ccccc2C(=O)C12CC2] |
-continued
| Compound Number | Structure |
|---|---|
| 740 | 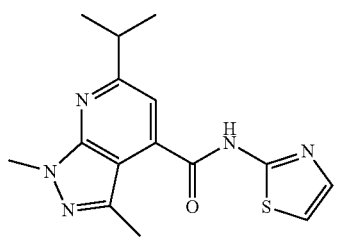 [SMILES: Cc1nn(C)c2nc(C(C)C)cc(C(=O)Nc3nccs3)c12] |
| 746 | 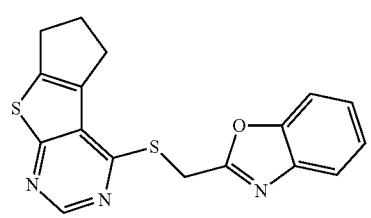 [SMILES: c1ccc2oc(CSc3ncnc4sc5c(c34)CCC5)nc2c1] |
| 749 | 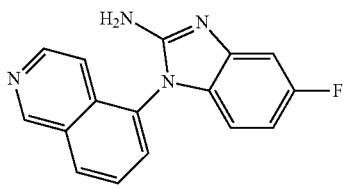 [SMILES: Nc1nc2cc(F)ccc2n1-c1cccc2cnccc12] |
| 753 | 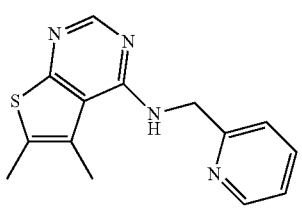 [SMILES: Cc1sc2ncnc(NCc3ccccn3)c2c1C] |
| 754 | 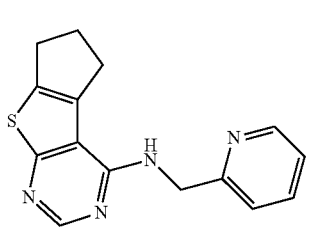 [SMILES: c1ccc(CNc2ncnc3sc4c(c23)CCC4)nc1] |
| 756 | 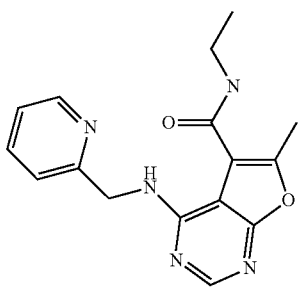 [SMILES: CCNC(=O)c1c(C)oc2ncnc(NCc3ccccn3)c12] |

| Compound Number | Structure |
|---|---|
| 758 | 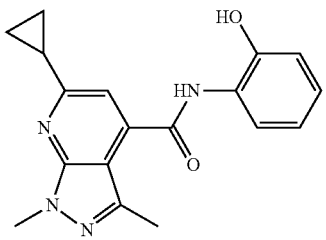 [SMILES: Cc1nn(C)c2nc(C3CC3)cc(C(=O)Nc3ccccc3O)c12] |
| 759 | 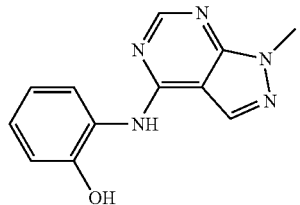 [SMILES: Cn1ncc2c(Nc3ccccc3O)ncnc21] |
| 767 | 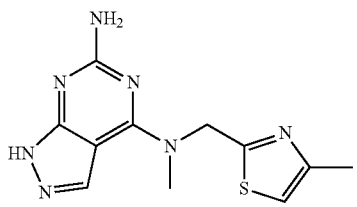 [SMILES: Cc1csc(CN(C)c2nc(N)nc3[nH]ncc23)n1] |
| 770 | 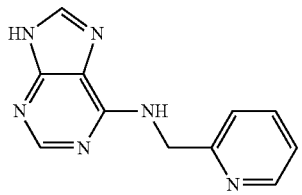 [SMILES: c1ccc(CNc2ncnc3[nH]cnc23)nc1] |
| 777 | 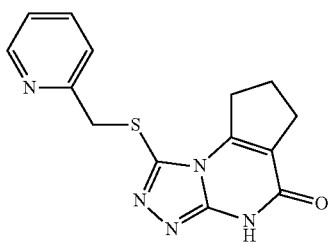 [SMILES: O=c1[nH]c2nnc(SCc3ccccn3)n2c2c1CCC2] |
| 778 | 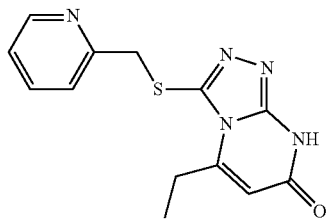 [SMILES: CCc1cc(=O)[nH]c2nnc(SCc3ccccn3)n12] |
| 784 | 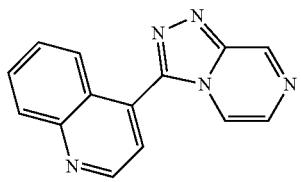 [SMILES: c1ccc2c(-c3nnc4cnccn34)ccnc2c1] |
| Compound Number | Structure |
|---|---|
| 785 | 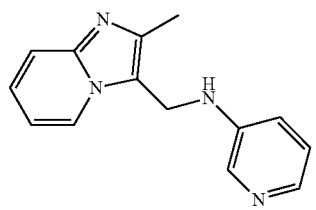 [SMILES: Cc1nc2ccccn2c1CNc1cccnc1] |
| 790 | 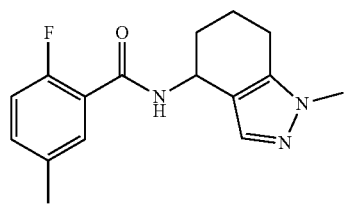 [SMILES: Cc1ccc(F)c(C(=O)NC2CCCc3c2cnn3C)c1] |
| 792 | 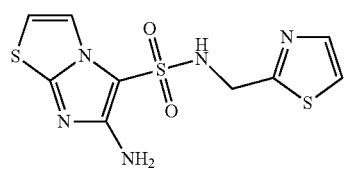 [SMILES: Nc1nc2sccn2c1S(=O)(=O)NCc1nccs1] |
| 796 | 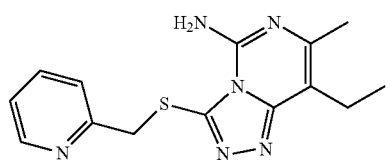 [SMILES: CCc1c(C)nc(N)n2c(SCc3ccccn3)nnc12] |
| 800 | 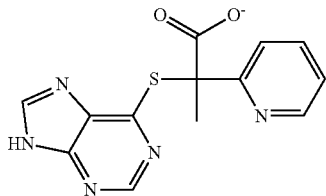 [SMILES: CC(Sc1ncnc2[nH]cnc12)(C(=O)[O-])c1ccccn1] |
| 801 | 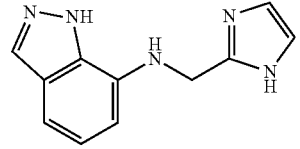 [SMILES: c1cc(NCc2ncc[nH]2)c2[nH]ncc2c1] |
| 804 | 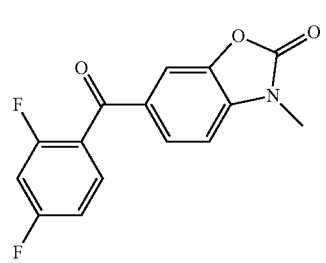 [SMILES: Cn1c(=O)oc2cc(C(=O)c3ccc(F)cc3F)ccc21] |

-continued

| Compound Number | Structure |
|---|---|
| 805 | 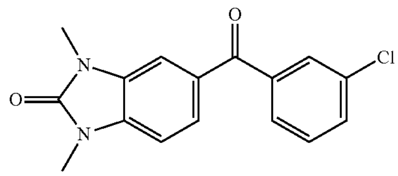 [SMILES: Cn1c(=O)n(C)c2cc(C(=O)c3cccc(Cl)c3)ccc21] |
| 808 | 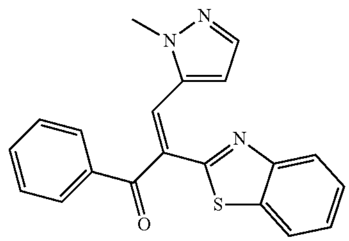 [SMILES: Cn1nccc1/C=C(/C(=O)c1ccccc1)c1nc2ccccc2s1] |
| 819 | 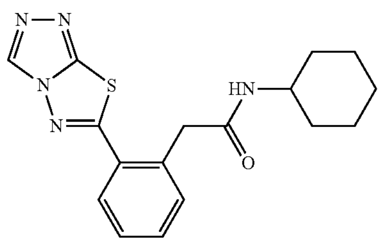 [SMILES: O=C(Cc1ccccc1-c1nn2cnnc2s1)NC1CCCCC1] |
| 821 | 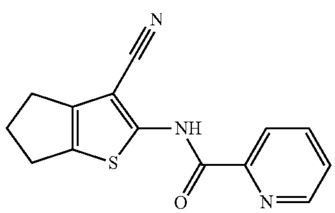 [SMILES: N#Cc1c(NC(=O)c2ccccn2)sc2c1CCC2] |
| 827 | 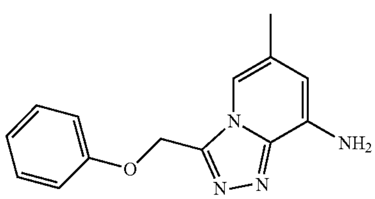 [SMILES: Cc1cc(N)c2nnc(COc3ccccc3)n2c1] |
| 828 | 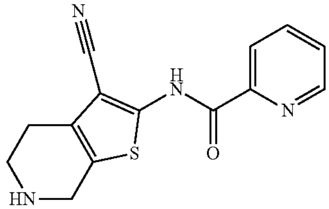 [SMILES: N#Cc1c(NC(=O)c2ccccn2)sc2c1CCNC2] |
| 831 | 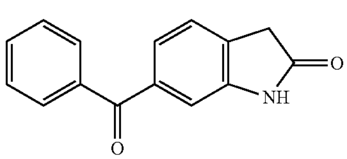 [SMILES: O=C1Cc2ccc(C(=O)c3ccccc3)cc2N1] |

-continued

| Compound Number | Structure |
|---|---|
| 833 | 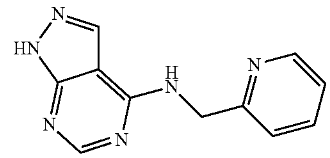 [SMILES: c1ccc(CNc2ncnc3[nH]ncc23)nc1] |
| 838 | 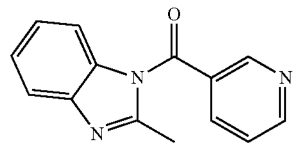 [SMILES: Cc1nc2ccccc2n1C(=O)c1cccnc1] |
| 844 | 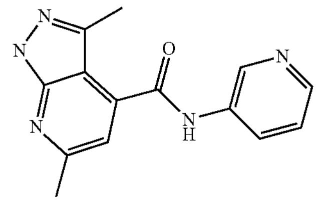 [SMILES: Cc1cc(C(=O)Nc2cccnc2)c2c(C)n[nH]c2n1] |
| 847 | 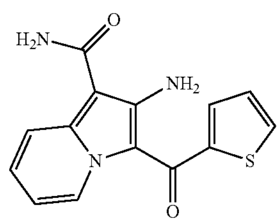 [SMILES: NC(=O)c1c(N)c(C(=O)c2cccs2)n2ccccc12] |
| 857 | 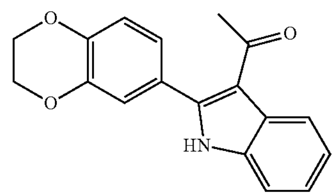 [SMILES: CC(=O)c1c(-c2ccc3c(c2)OCCO3)[nH]c2ccccc12] |
| 858 | 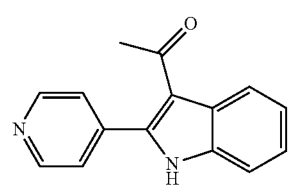 [SMILES: CC(=O)c1c(-c2ccncc2)[nH]c2ccccc12] |
| 869 | 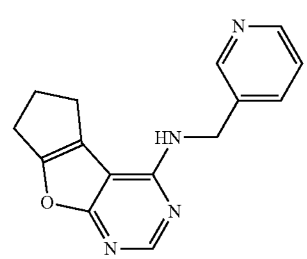 [SMILES: c1cncc(CNc2ncnc3oc4c(c23)CCC4)c1] |
| 872 | 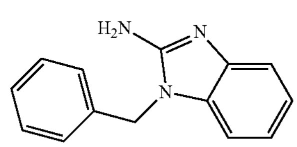 [SMILES: Nc1nc2ccccc2n1Cc1ccccc1] |

| Compound Number | Structure |
|---|---|
| 875 | 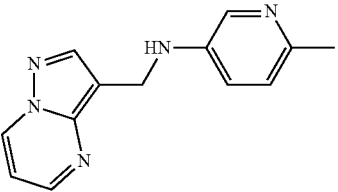 [SMILES: Cc1ccc(NCc2cnn3cccnc23)cn1] |
| 877 | 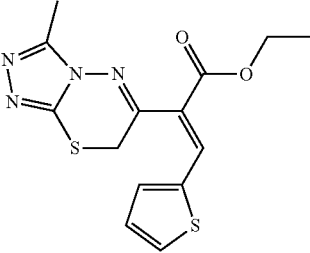 [SMILES: CCOC(=O)/C(=C/c1cccs1)C1=Nn2c(C)nnc2SC1] |
| 891 | 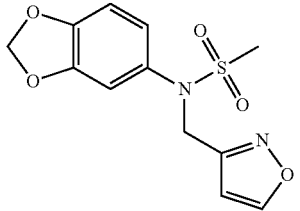 [SMILES: CS(=O)(=O)N(Cc1ccon1)c1ccc2c(c1)OCO2] |
| 910 | 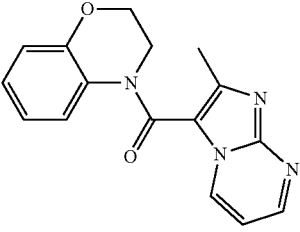 [SMILES: Cc1nc2ncccn2c1C(=O)N1CCOc2ccccc21] |
| 912 | 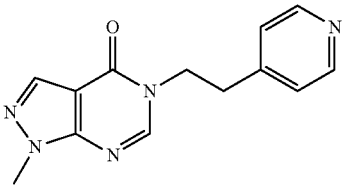 [SMILES: Cn1ncc2c(=O)n(CCc3ccncc3)cnc21] |
| 926 | 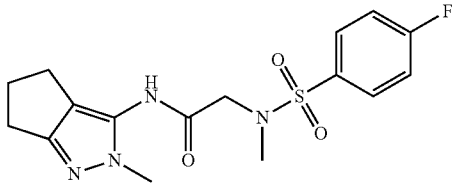 [SMILES: CN(CC(=O)Nc1c2c(nn1C)CCC2)S(=O)(=O)c1ccc(F)cc1] |
| 933 | 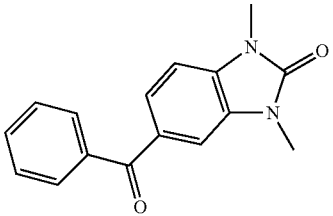 [SMILES: Cn1c(=O)n(C)c2cc(C(=O)c3ccccc3)ccc21] |
| 952 | 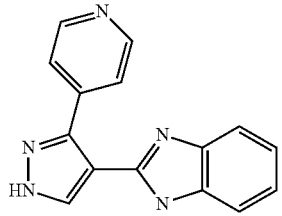 [SMILES: c1ccc2[nH]c(-c3c[nH]nc3-c3ccncc3)nc2c1] |
| 955 | 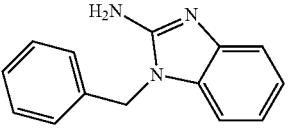 |
| 962 | 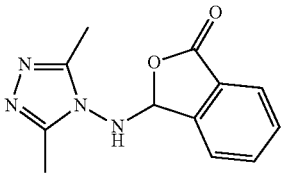 [SMILES: Cc1nnc(C)n1NC1OC(=O)c2ccccc21] |
| 963 | 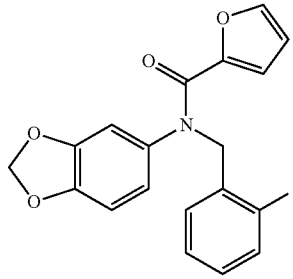 |
| 969 | 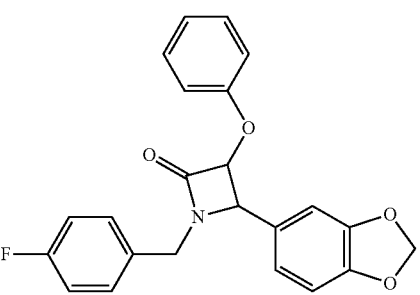 [SMILES: O=C1C(Oc2ccccc2)C(c2ccc3c(c2)OCO3)N1Cc1ccc(F)cc1] |

| Compound Number | Structure |
|---|---|
| 987 | (structure: indolizine with H₂N-C(=O)- group, NH₂, and 4-fluorobenzoyl substituents) |
| 990 | (structure: indolizine with O=C-NH₂ group, NH₂, and benzoyl substituents) |
| 999 | (structure: indole with H₂N-C(=O)- group, NH₂, and 4-fluorobenzoyl substituents) |

According to a further aspect of the invention, there is provided a compound of formula (IB) for use as a casein kinase 1 delta (CK1δ) inhibitor in the treatment of a neurodegenerative disorder, such as tauopathies.

According to certain aspects, for example, the compound for use as a casein kinase 1 delta (CK1δ) inhibitor in the treatment of a neurodegenerative disorder is 5-(1,3-benzoxazol-2-yl)-4-(pyridine-4-yl)pyrimidin-2-amine (Compound 324). In certain example aspects, the neurodegenerative disorder is a tauopathy, for example, Alzheimer's disease.

Compounds of formula 2-3, 26-28, 30-33, 35, 47-48, 51, 57-60, 63-64, 78, 84, 113, 123, 127-129, 145, 155-157, 171-173, 204, 206-207, 210, 225, 227, 233, 235-236, 241-242, 244, 249, 269, 285, 288, 303, 307-312, 314-316, 320, 324-325, 333, 336, 351, 357-360, 374-375, 384-391, 396, 399-402, 404-405, 407-411, 414, 424-425, 427-428, 437, 448, 456-457, 482, 484-485, 489-491, 495, 497-498, 505, 507, 516, 519, 524, 526, 553, 559-560, 568, 570, 575, 609, 615-616, 618, 626-627, 638, 653, 669, 692-694, 705, 709, 712, 716, 719, 725, 734, 738, 740, 746, 749, 753-754, 756, 758-759, 767, 770, 777, 784-785, 790, 792, 796, 800-801, 804-805, 808, 819, 821, 827-828, 831, 833, 838, 844, 847, 857-858, 869, 872, 875, 933, 952, 955, 969, 987, 990 or 999 are either commercially available or may be prepared in accordance with known synthetic procedures.

According to a further aspect of the invention there is provided a pharmaceutical composition comprising a compound of formula (IB) for use in the treatment of a neurodegenerative disorder, such as tauopathies.

In certain aspects, the pharmaceutical composition for use in the treatment of a neurodegenerative disorder comprises 5-(1,3-benzoxazol-2-yl)-4-(pyridine-4-yl)pyrimidin-2-amine (Compound 324). In certain example aspects, the neurodegenerative disorder is a tauopathy, for example, Alzheimer's disease.

The pharmaceutical compositions of the invention may comprise, in addition to one of the above substances, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may depend on the route of administration, e. g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant.

Liquid pharmaceutical compositions generally include a liquid carrier such as water, petroleum, animal or vegetable oils, mineral oil or synthetic oil.

Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The compounds of formula (IB) are believed to be casein kinase 1 delta (CK1δ) inhibitors. Certain compounds of formula (IB) have inhibitory activity of greater than 5%, in particular greater than 10%, more particularly greater than 25%, yet more particularly greater than 50%, especially greater than 75%, such as greater than 90%. Such compounds may be useful in the treatment in neurodegenerative disorders such as tauopathies. Tauopathies are conditions which are characterised by neurofibrillary tangles or aggregates of the tau protein. Tauopathies are a recognised class of conditions known to those skilled in the art and include Alzheimer's disease, frontotemporal dementia with Parkinsonism linked to chromosome 17 (FTDP-17), progressive supranuclear palsy (PSP), Pick's disease, corticobasal degeneration, multisystem atrophy (MSA), neurobasal degeneration with iron accumulation, type 1 (Hallervorden-Spatz), argyrophilic grain dementia, Down's syndrome, diffuse neurofibrillary tangles with calcification, dementia pugilistica, Gerstmann-Straussler-Scheinker disease, myotonic dystrophy, Niemann-Pick disease type C, progressive subcortical gliosis, prion protein cerebral amyloid angiopathy, tangle only dementia, postencephalitic parkinsonism, subacute sclerosing panencephalitis, Creutzfeldt-Jakob disease, amyotrophic lateral sclerosis/parkinsonism-dementia complex, non-Guamanian motor neuron disease with neurofibrillary tangles/dementia, and Parkinson's disease. The intracellular tau deposits are usually neuronal or glial and are filamentous and generally in a hyperphosphorylated state as compared to the level of phosphorylation in tau from control human brain. In the case of AD, this hyperphosphorylated tau is often referred to a paired helical filament tau (PHF) tau because it is derived from the PHF. In one embodiment, the tauopathy comprises Alzheimer's disease.

According to a further aspect of the invention, there is provided a method of treating a neurodegenerative disorder, such as tauopathies, which comprises administering a therapeutically effective amount of a compound of formula (IB).
Biological Data
1. CK1δ Inhibition Assay The compounds of the invention may be tested for inhibition of casein kinase 1 delta (CK1δ) in accordance with the assay protocols described in US 2010/0152157, EP 1,636,375 or Hanger et al (2007) J. Biol. Chem. 282, 23645-23654. In particular, the assay was conducted in accordance with the following protocol:
Reaction Buffer:

Base Reaction buffer; 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO It should be noted that required cofactors are added individually to each kinase reaction.
Reaction Procedure:
1. Prepare indicated substrate in freshly prepared Base Reaction Buffer as described above
2. Deliver any required cofactors to the substrate solution
3. Deliver indicated kinase into the substrate solution and gently mix
4. Deliver compounds in DMSO into the kinase reaction mixture
5. Deliver $^{33}$P-ATP (specific activity 0.01 μCi/μl final) into the reaction mixture to initiate the reaction
6. Incubate kinase reaction for 120 min. at room temperature
7. Reactions are spotted onto P81 ion exchange paper (Whatman #3698-915)
8. Wash filters extensively in 0.75% Phosphoric acid
Kinase Information:
CK1δ—Genbank Accession # NP_620693
Recombinant human full-length construct. GST-tagged, expressed in insect cells.
Final concentration in assay=4 nM
Substrate: CK1tide
Substrate sequence: [KRRRAL[pS]VASLPGL]
Final substrate concentration in assay=20 μM
It should be noted that no additional cofactors are added to the reaction mixture.

Compounds 30, 288, 314, 324-325, 336, 374, 391, 405, 615-616, 626, 705, 740, 753-754, 756, 759, 770, 784, 808, 819, 833, 844, 847, 869, 872, 875, 933, 952, 955, 969, 987, 990 and 999 were tested in the CK1δ inhibition assay and exhibited inhibition of greater than 5%.

In particular, compounds 324-325, 405, 754, 847, 952, 987, 990 and 999 exhibited inhibition of greater than 50%.

Yet more particularly, compounds 324, 952, 987, 990 and 999 exhibited inhibition of greater than 90%.
2. Measurement of Compound Effect on CK1δ-Mediated Tau Phosphorylation The in vivo phosphorylation of Tau protein is complex with a number of putative protein kinases involved. It is widely accepted that the kinases GSK3b and CDK5 are significant players in the generation of PHF Tau, the pathogenic form found in neurofibrillary tangles in Alzheimer's disease. More recently, there has been growing evidence supporting the role of other kinases, particularly CK1δ in Tau hyperphosphorylation in vivo. Hanger et al. 2007 (J. Biol. Chem. 282, 23645-23654) identified 37 phosphorylation sites in human PHF Tau and were able to recapitulate these in vitro using recombinant tau and various purified kinase preparations. These studies identified that certain sites were uniquely phosphorylated by CK1δ and that certain other sites required CK1δ and another kinase with CK1δ providing upstream phosphorylation to render the targeted site available for the second kinase. Thus, to assess whether candidate compounds selective inhibit CK1δ activity either directly or through blocking its priming for other kinases a number of different screens have been developed. The general concept of these screens is provided in WO2005/001114.

To measure the effect of putative CK1δ inhibitors on the levels of CK1δ-mediated phosphorylation selected-reaction monitoring assays were performed that provide quantitative relative measurement of phosphate group occupancy at specific sites in transgenic human and endogenous murine forms of Tau.

The PhosphoTau SRM V2 assay measures total tau and relative phosphorylation levels at five of the most commonly studied sites on Tau and was obtained from Proteome Sciences plc (Cobham, England). None of the sites in the V2 assay is uniquely phosphorylated by CK1δ and there is a possibility that compound-induced inhibition of phosphorylation measured by this method may be achieved through promiscuous inhibition of other kinases such as GSK3b and/or CDK5. To address this limitation, Proteome Sciences has developed a V3 assay that measures total tau and two sites that are exclusively phosphorylated by CK1δ in addition to four others that have been shown to be phosphorylated in vitro by at least one other Tau kinase in addition to CK1δ. Table 1 lists the various sites covered and the candidate Tau kinases reported in Hanger et al. (2007).

TABLE 1

Tau phosphorylation sites covered by Tau Phosphorylation SRM V2 and V3 assays

| Site number | Candidate Kinases |
| --- | --- |
| Assay V2 | |
| Ser181 | GSK3b |
| Ser199 | CK2, GSK3b, PKA |
| Thr231 | GSK3b, PKA |
| Ser262 | CK1δ, GSK3b, PKA |
| Ser396 | CK1δ, CK2, GSK3b |
| Assay V3 | |
| Ser46 | CK1δ, GSK3b |
| Thr50 | CK1δ, GSK3b |
| Ser113* | CK1δ |
| Ser396 | CK1δ, CK2, GSK3b |
| Ser404 | CK1δ, CK2, GSK3b |
| Ser433* | CK1δ |

Numbering based on human 2N4R tau.
*CK1δ unique site

SH-SY5Y-TM HT Cell Line

The SH-SY5Y-TMHT cell line (JSW Life Sciences, Graz, Austria) represents an in vitro model of tauopathy. The cell line is created by stably transfecting the human neuroblastoma derived SH-SY5Y cell line with a vector containing the full length human 2N4R Tau isoform which carries two common disease associated mutations (V337M/R406W). In recent studies (Flunkert et al. 2011 submitted, Loeffler et al. 2011 submitted) both the SH-SY5Y-TMHT cell line and a transgenic mouse line carrying the same human transgene were shown to express high levels of human Tau which becomes hyperphosphorylated at multiple epitopes previously demonstrated to be phosphorylated in various human tauopathies including Alzheimer's disease. Furthermore, in SH-SY5Y-TMHT cells exposed to different kinase inhibitors, including JNK-Inhibitor SP600125, and CK1 inhibitor IC261 levels of Tau phosphorylation at key pathogenic sites were reduced in patterns consistent with the known sitespecificity of the targeted kinase. Thus, the SH-SY5Y-TMHT cell line is ideally suited to the screening of novel Tau kinase inhibitors.

Compound Screening in SH-SY5Y-TMHT Cells

SH-SY5Y-TMHT cells are kept in culture medium (DMEM medium, 10% FCS, 1% NEAA, 1% L-Glutamine, 100 µg/ml Gentamycin, 300 µg/ml Geneticin G-418) for 2 days until 80-90% confluency. Cells are then differentiated in culture medium supplemented with 10 µM retinoic acid (RA) for 7 days changing medium every 2 to 3 days. Differentiated cells are seeded onto 6-well plates and 96-well plates at a cell density of $1.25 \times 10^6$ and $8 \times 10^5$ cells per well, respectively. On day 8 post-differentiation, the test compounds, reference compounds and vehicle control were added to the culture medium. After 6 h of compound exposure one plate of cells is subjected to a MTT assay to evaluate the effect of test and reference items on cell viability. Remaining wells are washed once with cold PBS and harvested in 300 µl RIPA-Buffer [50 mM Tris pH 7.4, 1% Nonident P40, 0.25% Na-deoxy-cholate, 150 mM NaCl, 1 mM EDTA, 1 µM NaF, 1 µM Na-ortho-vanadate, 80 mM Glycerophosphate, supplemented with freshly added protease (Calbiochem) and phosphatase (Sigma) inhibitor cocktail]. The cell suspension is transferred into a 1.5 ml tube and additionally lysed by sonication on ice. An aliquot of 20 µl is taken for the determination of the protein concentration (BCA assay). Subsequently, the lysates are snap frozen and stored at −80° C. until shipment.

Two independent experiments in three (four) technical replicates are performed as depicted in Table 2.

TABLE 2

| Experiment | Cells | Treatment | Concentration | Evaluation | |
|---|---|---|---|---|---|
| ExpA | SH-SY5Y-TMHT | Vehicle | — | MTT | BSA |
| | | Compound 324 | 10-5-1-0.5-0.1-0.05 µM | | TauP V2 |
| | | Compound 987 | 10-5-1-0.5-0.1-0.05 µM | | TauP V3 |
| | | PF670462 | 1-0.5-0.1 µM | | |
| ExpB | SH-SY5Y-TMHT | Vehicle | — | MTT | BSA |
| | | Compound 324 | 10-5-1-0.5-0.1-0.05 µM | | TauP V2 |
| | | Compound 987 | 10-5-1-0.5-0.1-0.05 µM | | TauP V3 |
| | | PF670462 | 1-0.5-0.1 µM | | |

Cell Viability Testing

To determine compound activity, it is necessary to control for potential cell toxicity of all molecules. Viability of cultures is determined by the MTT assay. This assay allows the measurement of the mitochondrial dehydrogenase activity which reduces yellow MTT to dark blue formazan crystals. Since this reaction is catalyzed in living cells only this assay is used for the determination of cell viability. MTT solution is added to each well in a final concentration of 0.5 mg/ml. After 2 hours, the MTT containing medium is aspired. Cells are lysed in 3% SDS and the formazan crystals are dissolved in isopropanol/HCl. Optical density is measured with a plate-reader at wavelength 570 nm. Cell survival rate is expressed as optical density (OD). Values are calculated as percent of control values.

Quantitative Determination of Total Protein Content

Prior to assessment of specific Tau phosphorylation status the concentration of total protein in each cell lysate is determined using a standard BCA assay (Pierce Biotechnology, Rockford, USA). Briefly, 20 µl of cell lysate was used in the assay according to the manufacturer's instructions.

Quantitative Determination of Total Tau & Phosphorylated Tau

Mass Spectrometric Assays

Total cell lysates from TMHT cell lines treated with Compound 324, comparative compounds Compound 987, (2-amino-3-[(4-fluorophenyl)carbonyl]indolizine-1-carboxamide) and PF670462 and relevant vehicle control respectively are first subjected to 1-dimensional SDS-PAGE to purify the protein fraction. Stacking gels are loaded with approximately 100 µg total protein based on BCA assay results. Gels are run until the total protein content forms a single discrete band in the stacking gel. Each protein band is then cut from the gel and digested with either trypsin or Asp-N and analysed using the PhosphoTau SRM assay V2 or V3 respectively. Each assay method quantifies the phosphorylation in pre-clinical material using a triple quadrupole mass spectrometer (TSQ Vantage, Thermo Scientific, Hemel Hempstead, UK). Prior to SRM analysis phosphopeptides and pre-clinical samples were resolved by RP-chromatography (XBridge column, Waters, Manchester, UK) over a 9 minute gradient 0-30% ACN (buffer A; 0.1% FA, buffer B; ACN, 0.1% FA). Light and heavy versions for each peptide and phosphopeptide were monitored by several SRM transitions, using optimised S Lens values and collision energy settings. The area under the SRM LC peak was used to quantitate the amount of analyte present in each cell lysate as a single point reference to the signal of the heavy peptide spike.

An 11 point calibration curve of light phosphopeptides with each point in the curve spiked with 100 fmol heavy phosphopeptides was also produced to determine assay characteristics (LOD, LOQ, precision and accuracy). For each specified tau population, the endogenous level of each tau phosphopeptide was quantified against its calibration curve (0.25-1000 fmol on column). Prior to LC-SRM analysis each tau population was spiked with 100 fmol of the heavy phosphopeptide standards. All data was processed using Pinpoint software (Thermo Scientific) and results reported as µg phospho-peptide/µg total protein.

Western Blotting

Lysates of treated cells were prepared in Laemmli buffer and 10 µg loaded into each lane of a 10% Nu-PAGE gel (Invitrogen, UK). Samples were run until the coomassie blue dye fromt was within 1 cm of the bottom of the gel. The separated proteins were transferred onto nitrocellulose and blots developed using antibodies specific for total tau (Polyclonal Rabbit Anti-Human Tau, Dako, UK (cat # A0024)) and phopho-Threonine 231 (Tau (Phospho-Thr231) Antibody, Signalway Antibody, USA (cat # 11110)) respectively. In each case the bound antibody was detected using ECL Rabbit IgG, HRP-Linked (from donkey) (GE Healthcare, UK (cat # NA934))

Results

Figure 2:
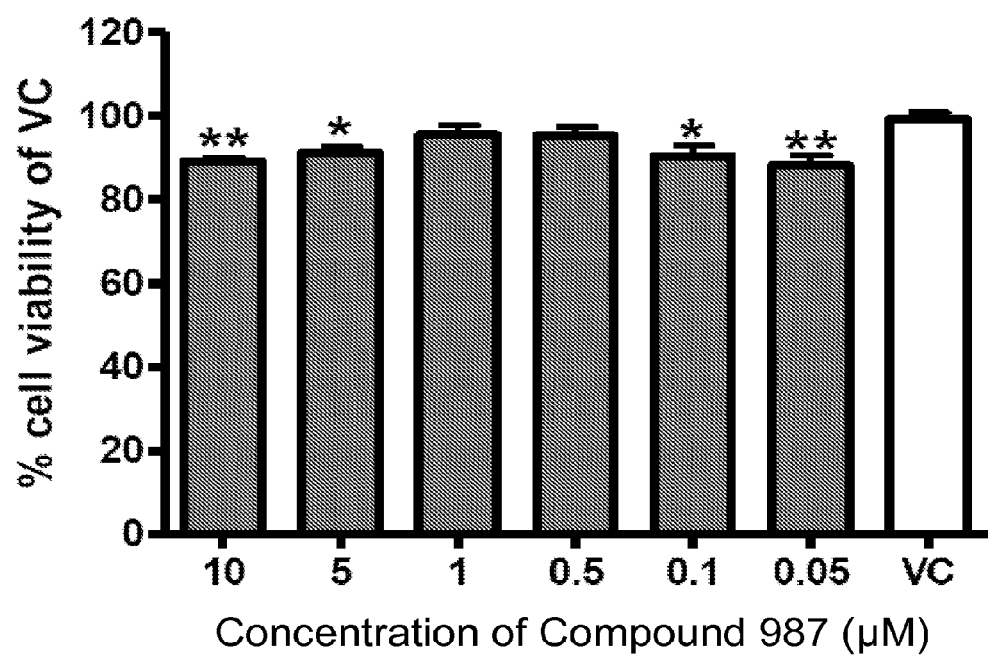
FIG. 2 shows the effect of Compound 987 on the cell viability of SH-SY5Y-TMHT cells.
Figure 3:
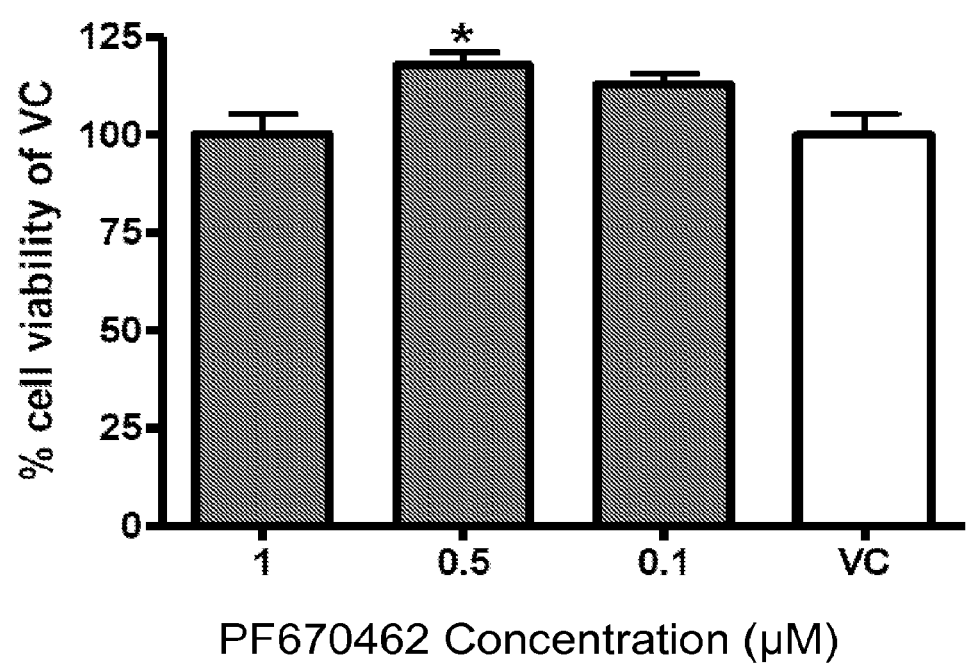
FIG. 3 shows the effect of PF670462 on the cell viability of SH-SY5Y-TMHT cells.

Effect of Test and Reference Compounds on the Cell Viability of SH-SY5Y-TMHT Cells Cell viability was determined in differentiated SH-SY5Y-TMHT cells by the MTT assay. Test and reference compounds were applied in a concentration range from 0.05 µM to 10 µM and from 0.1 µM to 1 µM, respectively. Upon 6 h of treatment, cell viability was evaluated. FIG. 1 shows the effect of Compound 324 on the cell viability of SH-SY5Y-TMHT cells wherein the graph represents effect of Compound 324 on cell viability of SH-SY5Y-TMHT cells in % of the vehicle control (VC, white bar). Statistical significance is indicated by $*<0.05$, $<0.01$, $*<0.001$ as determined by One-Way ANOVA. Data are shown from two independent experiments as group mean+/−SEM (n=8). It can be seen from FIG. 1 that Compound 324 exhibited a protective effect on the cell viability of SH-SY5Y-TMHT cells in a dose dependent manner although the effect was only statistically significant at a concentration of 10 μM. FIG. 2 shows the effect of Compound 987 on the cell viability of SH-SY5Y-TMHT cells wherein the graph represents effect of Compound 987 on cell viability of SH-SY5Y-TMHT cells in % of the vehicle control (VC, white bar). Statistical significance is indicated by *<0.05, <0.01, *<0.001 as determined by One-Way ANOVA. Data are shown from two independent experiments as group mean+/−SEM (n=8). It can be seen from FIG. 2 that Compound 987 decreased the cell viability in the lower and higher concentration range. At a concentration of 1 and 0.5 μM no cytotoxic effect was observed. FIG. 3 shows the effect of PF670462 on the cell viability of SH-SY5Y-TMHT cells wherein the graph represents effect of PF670462 on cell viability of SH-SY5Y-TMHT cells in % of the vehicle control (VC, white bar). Statistical significance is indicated by *<0.05, <0.01, *<0.001 as determined by One-Way ANOVA. Data are shown from two independent experiments as group mean+/−SEM (n=8). It can be seen from FIG. 3 that the reference compound PF 670462 only displayed a significant protective effect on the cell viability of SH-SY5Y-TMHT cells at a concentration of 0.5 μM.

Protein Determination of SH-SY5Y-TMHT Cells Following Treatment

Protein concentration of cell lysates of the treated SH-SY5Y-TMHT cells was determined using a standard BCA assay. Protein amount was determined from all samples in duplicates. The protein concentration of the samples was in the expected range according to the amount of cells seeded per 12-well plate ranging between 150-350 μg/ml.

Determination of Compound Treatment Effect on Specific Phosphorylation Sites

Mass Spectrometric Assay

Figure 4:
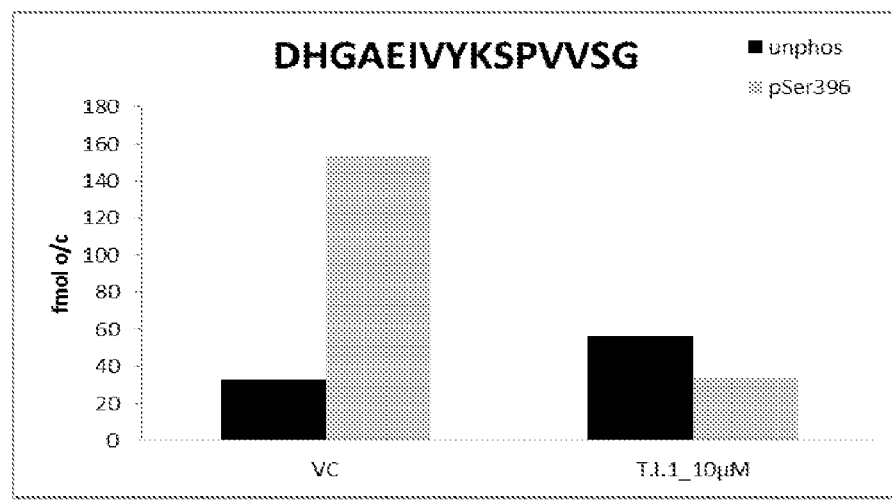
FIG. 4 including panels A and B shows reduction of phosphorylation of Serine 396. Panels A and B are sometimes referred to herein in the collective as FIG. 4.
Figure 4:
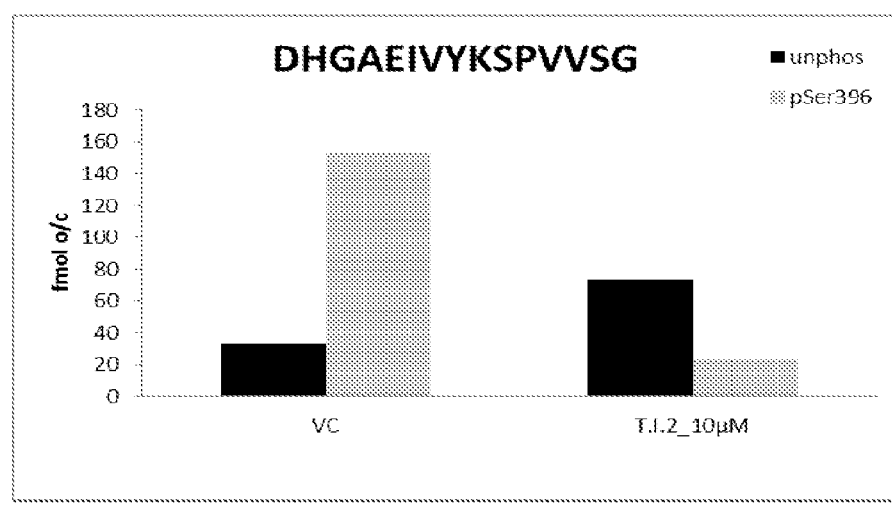

Testing of SH-SY5Y-TMHT cell lysates was performed using the PhosphoTau SRM assay V2 and V3. When the relative level of phosphorylation at each site is compared with the ratio in vehicle treated controls there was a distinct reduction in the level of phosphopeptide in cells treated with Compound 324 (data shown for 10 μM) and comparative compound 2-amino-3-[(4-fluorophenyl)carbonyl]indolizine-1-carboxamide (Compound 987) (data shown for 10 μM). An example showing reduction of phosphorylation on Serine 396 is shown in FIG. 4. This Figure shows mass spectrometric determination of CK1δ-selective compounds on phosphorylation of Serine 396 in SH-SY5Y-TMHT cells. Panel A shows cells treated with Vehicle Control (VC) or Compound 324 (T.I.1_10 μM) and Panel B shows cells treated with Vehicle Control (VC) or Compound 987 (T.I.2_10 μM).

In cells exposed to the vehicle control approximately 83% of Tau is phosphorylated at S396. Treatment with 10 μM Compound 324 reduced this to 38% whilst 10 μM Compound 987 reduced pS396 levels to 24%. These results confirm the inhibition of pS396 by CK1δ selective reagents.

Western Blot Assay

Figure 5:
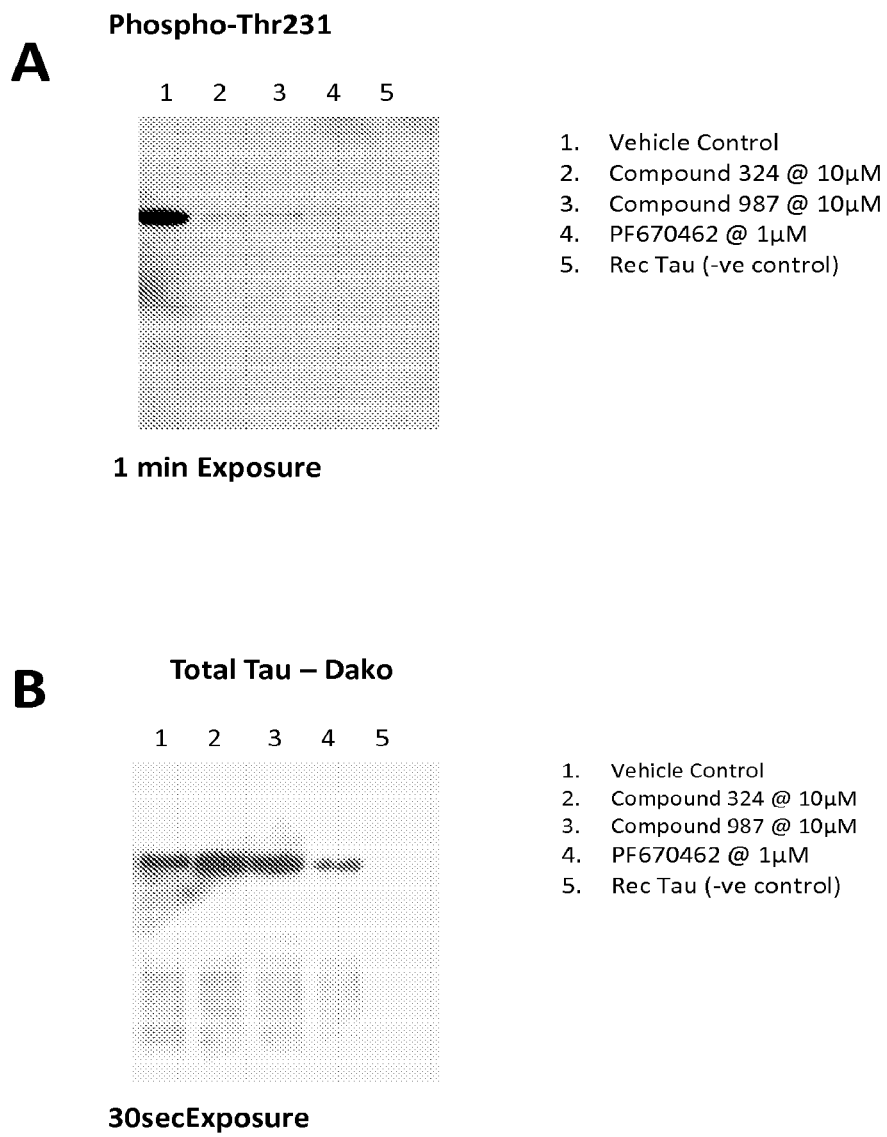
FIG. 5 shows the Western Blot measurement of pT231 (panel A) and total Tau (panel B) levels in SH-SY5Y-TMHT cells treated with selective CK1d inhibitors. Panels A and B are sometimes referred to herein in the collective as FIG. 5.

Levels of total Tau and Tau phosphorylated at Threonine 231 in SH-SY5Y-TMHT cell lysates treated with vehicle control, Compound 394 (10 μM), comparative compounds Compound 987 (10 μM) and PF670462 (5 μM) were quantified by Western Blotting. FIG. 5 shows the Western Blot measurement of pT231 (panel A) and total Tau (panel B) levels in SH-SY5Y-TMHT cells treated with selective CK1δ inhibitors. As shown in FIG. 5, all three compounds reduced the detectable level of pT231 in Tau protein whereas this epitope was strongly present in vehicle-treated cells. There was no significant difference in the detectable levels of total Tau between the preparations other than for the PF670462-treated lysate which appeared to contain marginally less total Tau than the others. These results confirm the inhibition of pT231 by CK1δ selective reagents.

The invention claimed is:

1. A method of treating Alzheimer's disease in a subject, comprising:
   administering a therapeutically effective amount of a pharmaceutical composition comprising 5-(1,3-benzoxazol-2-yl)-4-(pyridine-4-yl)pyrimidin-2-amine (Compound 324), or a pharmaceutically acceptable salt or solvate thereof, to the subject; and
   treating Alzheimer's disease in the subject.

2. The method of claim 1, wherein the pharmaceutical composition is a tablet, capsule, powder or liquid.

3. The method of claim 1, wherein the pharmaceutical composition is for oral administration.

4. The method of claim 1, wherein the pharmaceutical composition is for intravenous, cutaneous or subcutaneous, nasal, intramuscular, or intraperitoneal administration.

5. The method of claim 1, wherein the pharmaceutical composition is a liquid.

6. The method of claim 1, wherein the pharmaceutical composition further comprises at least one pharmaceutically acceptable excipient, carrier, buffer, or stabilizer.

7. The method of claim 1, wherein the pharmaceutical composition is a parenterally-acceptable aqueous solution.

8. The method of claim 1, wherein the amount of Compound 324 administered to the patient is sufficient to reduce phosphorylation on S396 of a Tau protein in at least one cell of the patient.

* * * * *